(12) United States Patent
Vardon et al.

(10) Patent No.: US 10,486,141 B2
(45) Date of Patent: Nov. 26, 2019

(54) SOLID CATALYSTS FOR PRODUCING ALCOHOLS AND METHODS OF MAKING THE SAME

(71) Applicant: Energy, United States Department of, Washington, DC (US)

(72) Inventors: Derek R. Vardon, Lakewood, CO (US); Todd R. Eaton, Denver, CO (US); Amy Settle, Wheat Ridge, CO (US)

(73) Assignee: U.S. Department of Energy, Washington, DC (US)

( * ) Notice: Subject to any disclaimer, the term of this patent is extended or adjusted under 35 U.S.C. 154(b) by 0 days.

(21) Appl. No.: 15/828,658

(22) Filed: Dec. 1, 2017

(65) Prior Publication Data
US 2019/0168190 A1 Jun. 6, 2019

(51) Int. Cl.
| | | |
|---|---|---|
| *B01J 23/42* | (2006.01) | |
| *B01J 23/44* | (2006.01) | |
| *B01J 21/18* | (2006.01) | |
| *B01J 23/62* | (2006.01) | |
| *B01J 23/46* | (2006.01) | |
| *B01J 27/20* | (2006.01) | |
| *B01J 35/10* | (2006.01) | |
| *C07C 31/20* | (2006.01) | |
| *C07C 29/149* | (2006.01) | |
| *C07C 31/08* | (2006.01) | |
| *C07C 31/10* | (2006.01) | |

(52) U.S. Cl.
CPC .......... *B01J 23/626* (2013.01); *B01J 23/462* (2013.01); *B01J 27/20* (2013.01); *B01J 35/1014* (2013.01); *B01J 35/1019* (2013.01); *B01J 35/1023* (2013.01); *C07C 29/149* (2013.01); *C07C 31/08* (2013.01); *C07C 31/10* (2013.01); *C07C 31/205* (2013.01); *C07C 31/207* (2013.01)

(58) Field of Classification Search
CPC . B01J 23/42; B01J 23/44; B01J 23/462; B01J 23/626; B01J 23/6525; B01J 23/6527; B01J 23/6567; B01J 23/8913; B01J 21/18
USPC ................ 502/310, 314, 316, 326, 182, 185
See application file for complete search history.

(56) References Cited

U.S. PATENT DOCUMENTS

| | | | | |
|---|---|---|---|---|
| 5,478,952 A * | 12/1995 | Schwartz | ............. | B01J 23/6567 549/325 |
| 6,008,384 A * | 12/1999 | Bockrath | ............. | C07C 29/149 502/185 |
| 6,495,730 B1 * | 12/2002 | Konishi | ................... | B01J 21/18 568/831 |
| 2010/0029995 A1 * | 2/2010 | Johnston | .................. | B01J 21/08 568/840 |
| 2010/0197486 A1 * | 8/2010 | Johnston | .................. | B01J 23/42 502/241 |

(Continued)

*Primary Examiner* — Patricia L. Hailey
(74) *Attorney, Agent, or Firm* — Felisa L. Leisinger; Michael J. Dobbs; Brian J. Lally

(57) ABSTRACT

An aspect of the present disclosure is a catalyst that includes a solid support, a first metal that includes at least one of ruthenium (Ru), platinum (Pt), palladium (Pd) deposited on the solid support, and a second metal comprising at least one of tin (Sn), rhenium (Re), cobalt (Co), molybdenum (Mo), or tungsten (W) deposited on the solid support, where the first metal and the second metal are present at a first metal to second metal mass ratio between about 1.0:2.0 and about 1.0:0.5.

20 Claims, 23 Drawing Sheets

(56) References Cited

U.S. PATENT DOCUMENTS

| | | | |
|---|---|---|---|
| 2011/0082322 A1* | 4/2011 | Jevtic | C07C 29/149 568/885 |
| 2012/0209034 A1* | 8/2012 | Zhou | B01J 23/002 568/885 |
| 2013/0225878 A1* | 8/2013 | Weiner | B01J 23/835 568/885 |
| 2013/0245335 A1* | 9/2013 | Zhou | B01J 37/0205 568/885 |
| 2014/0051894 A1* | 2/2014 | Weiner | C07C 29/149 568/885 |
| 2016/0200646 A1* | 7/2016 | Murphy | C07C 29/149 568/864 |

* cited by examiner

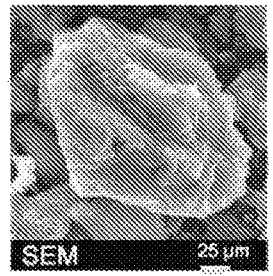 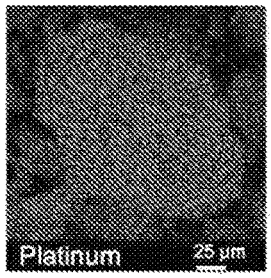 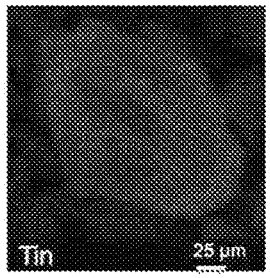 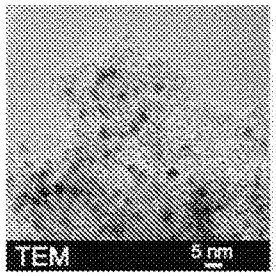
FIG. 5A　　　　FIG. 5B　　　　FIG 5C　　　　FIG 5D
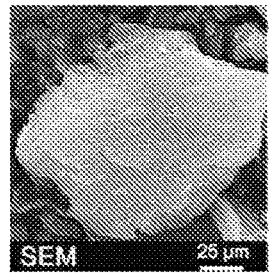 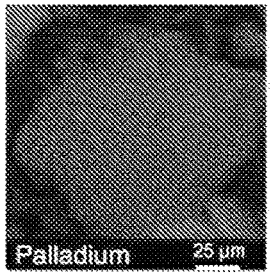 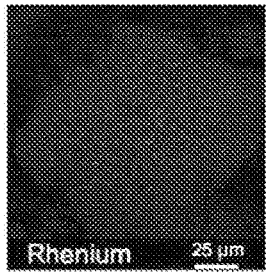 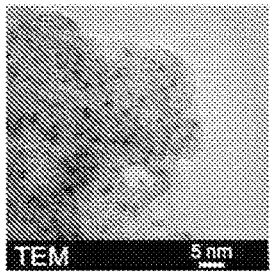
FIG. 5E　　　　FIG. 5F　　　　FIG 5G　　　　FIG 5H
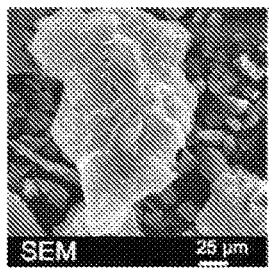 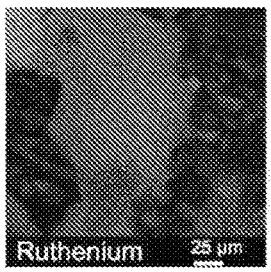 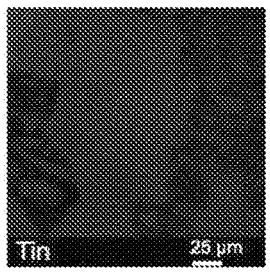 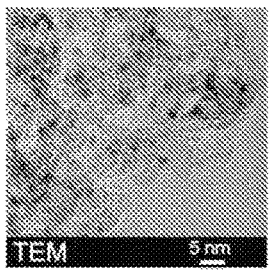
FIG. 5I　　　　FIG. 5J　　　　FIG 5K　　　　FIG 5L

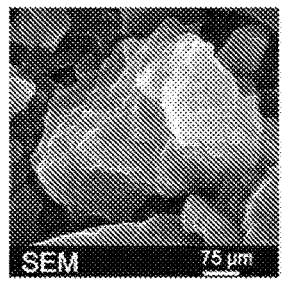 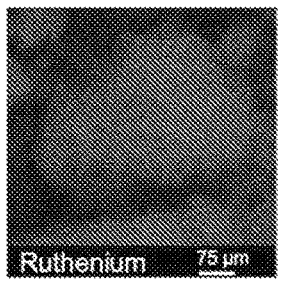 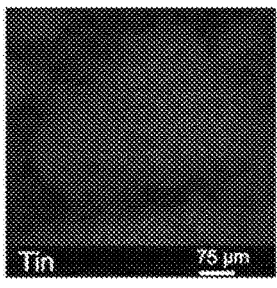 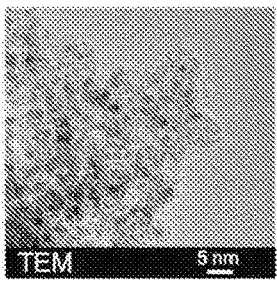
FIG. 10A          FIG. 10B          FIG. 10C          FIG. 10D
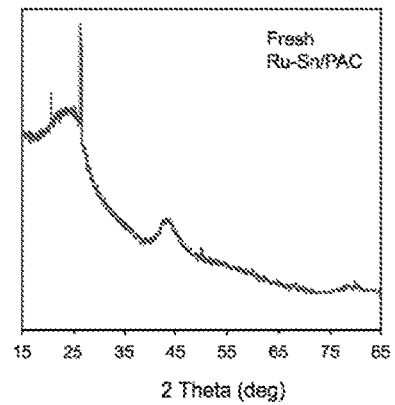 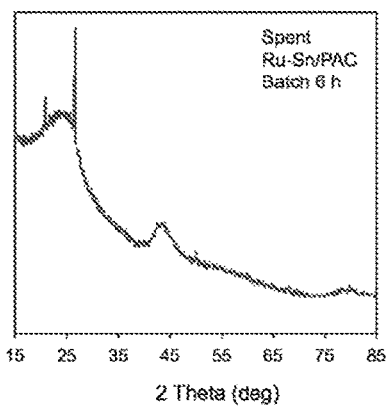
FIG. 10E          FIG. 10F

US 10,486,141 B2

SOLID CATALYSTS FOR PRODUCING ALCOHOLS AND METHODS OF MAKING THE SAME

GOVERNMENT INTEREST

The United States Government has rights in this disclosure under Contract No. DE-AC36-08GO28308 between the United States Department of Energy and the Alliance for Sustainable Energy, LLC, the Manager and Operator of the National Renewable Energy Laboratory.

FIELD OF THE INVENTION

One or more embodiments relate to solid bimetallic catalysts for the reduction of carboxylic acids and/or ketones to alcohols.

BACKGROUND

With the increasing pressures of climate change, renewable alternatives are needed to displace our dependence on petroleum. Succinic acid is one such platform chemical that may be produced at the industrial scale from the biological conversion of refined sugars, as well as through several robust, native succinic-acid producing microbes from lignocellulosic sugars. Following biological production, succinic acid may be catalytically converted to expand its potential market applications. Of note, succinic acid can be catalytically reduced to 1,4-butanediol (BDO), which has a market value of $3.50 per kg (2011 USD) and an annual demand of over 1,370,000 tonnes. BDO is heavily used in the plastic industry for numerous applications including polyesters, polyurethanes, and polyethers. Preliminary life cycle analysis has also shown that succinic acid-derived BDO has potential to reduce greenhouse gas emissions when compared to petrochemical routes for BDO production. Thus, catalysts that enable the efficient and/or high-yield conversion of succinic acid to BDO remains a desirable objective for enabling the conversion of bio-based intermediates to useful fuels and/or chemicals. Monocarboxylic acids, such as acetic acid, lactic acid, propionic acid, and butyric acid, can be produced at high titers from fermentation of lignocellulosic sugars and the corresponding alcohols produced by hydrogenation are useful fuels and/or chemicals, such as ethanol, propanediol, n-propanol, and n-butanol. For example, propionic acid can be reduced to n-propanol. Propanol is versatile three-carbon molecule, which can further be catalytically transformed to value-added chemicals like acrylonitrile ($2.75 per kg, 2008 USD), polypropylene ($1.50 per kg, 2008 USD), and propylene oxide ($2.21 per kg, 2008 USD), all via a propylene intermediate. The routes towards producing these value-added chemicals in an economically feasible way rely heavily on a high-yielding hydrogenation step to convert propionic acid to n-propanol.

SUMMARY

According to one aspect of the invention, a catalyst that comprises a solid support, a first metal deposited on the solid support, and a second metal deposited on the solid support. The first metal includes at least one of ruthenium (Ru), platinum (Pt), or palladium (Pd). The second metal includes at least one of tin (Sn), rhenium (Re), cobalt (Co), molybdenum (Mo), or tungsten (W). The first metal and the second metal are present at a first metal to second metal mass ratio between about 1.0:2.0 and about 1.0:0.5. The hydrogen, carboxylic acid, and catalyst are contacted such that at least a portion of the carboxylic acid is converted to an alcohol.

In another aspect of the invention, a method comprising the steps of providing hydrogen, providing carboxylic acid, and providing a catalyst. The catalyst comprises a solid support, a first metal deposited on the solid support, and a second metal deposited on the solid support. The first metal includes at least one of ruthenium (Ru), platinum (Pt), or palladium (Pd). The second metal includes at least one of tin (Sn), rhenium (Re), cobalt (Co), molybdenum (Mo), or tungsten (W). The first metal and the second metal are present at a first metal to second metal mass ratio between about 0.5:1.0 and about 2.0:1.0. The hydrogen, carboxylic acid, and catalyst are contacted such that at least a portion of the carboxylic acid is converted to an alcohol.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in referenced figures of the drawings. It is intended that the embodiments and figures disclosed herein are to be considered illustrative rather than limiting.

FIGS. 5A-5D illustrate SEM-EDS and TEM characterization data of fresh 1.0:1.0 Pt—Sn/PAC, according to some embodiments of the present disclosure.

FIGS. 5E-5H illustrate SEM-EDS and TEM characterization data of fresh 1.0:1.0 Pd—Re/PAC, according to some embodiments of the present disclosure.

FIGS. 5I-5L illustrate SEM-EDS and TEM characterization data of fresh 1.0:1.0 Ru—Sn/PAC, according to some embodiments of the present disclosure.

FIGS. 10A-10F illustrate characterization data of spent Ru—Sn/PAC (1.0:1.0) used in the batch reactor 6-h screening study by SEM-EDS (FIGS. 10A-10C), TEM (FIG. 10D), and XRD for the fresh (FIG. 10E) and spent catalyst (FIG. 10F), according to some embodiments of the present disclosure.

DETAILED DESCRIPTION

The present disclosure may address one or more of the problems and deficiencies of the prior art discussed above. However, it is contemplated that some embodiments as disclosed herein may prove useful in addressing problems and deficiencies in a number of other technical areas. Therefore, the embodiments described herein should not necessarily be construed as limited to addressing any of the particular problems or deficiencies discussed herein.

The present disclosure relates to solid bimetallic catalysts for the reduction of carboxylic acids and/or ketones to alcohols. For example, in some embodiments of the present disclosure, a Ru—Sn bimetallic catalyst supported on an activated carbon (AC) may be utilized for the aqueous phase reduction of succinic acid to 1,4-butanediol (BDO), the reduction of propionic acid to 1-propanol, the reduction of lactic acid to 1,2-propanediol, the reduction of acetic acid to ethanol, the reduction of adipic acid to 1,6-hexanediol, the reduction of 4-heptanone to 4-heptanol, and/or the reduction of 6-undecanone to 6-undecanol. In some embodiments of the present disclosure, a Ru—Sn bimetallic catalyst supported on an AC may be utilized for the aqueous phase reduction reactions of at least one of butyric acid to butanol, pentanoic acid to pentanol, and/or hexanoic acid to heptanol. In some embodiments of the present disclosure, a Ru—Sn bimetallic catalyst supported on an AC may be utilized for the aqueous phase reduction reaction of at least one of lactic acid, levulinic acid, hydroxy-butyric acid, and/or 3-hydroxy-propionic acid to 1,3-propanediol. In some of the present disclosure, a Ru—Sn bimetallic catalyst supported on an AC may be utilized for the aqueous phase reduction reactions of at least one of acetone to isopropanol, pentanone to pentanol, and/or nonanone to nonanol. In general, a bimetallic catalyst may be used for the aqueous phase reduction of at least one of a short chain anaerobic acid, a hydroxyacid, a long chain fatty acid, and/or a short chain ketone to an alcohol.

Figure 1:
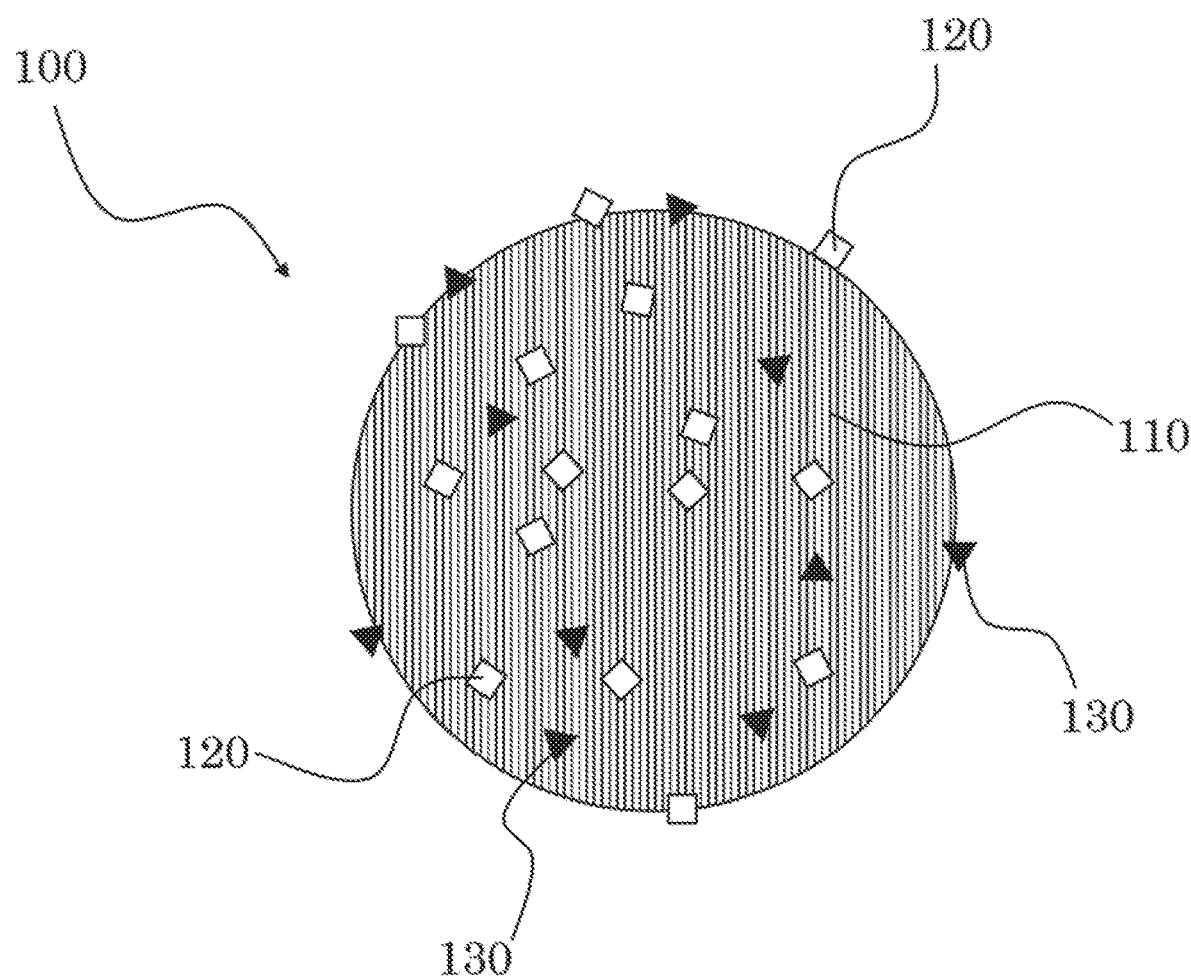
FIG. 1 illustrates a catalyst for reacting a carboxylic acid and hydrogen to form an alcohol, according to some embodiments of the present disclosure.

Referring to FIG. 1, a catalyst 100 is illustrated that includes a first metal 120 and a second metal 130 deposited on a surface of a solid support 110. Thus, a catalyst 100 may be in a solid phase that includes a solid support 110 such as an activated carbon, an oxide, and/or an aluminosilicate. Examples of oxide solid supports include materials like $SiO_2$, $TiO_2$, $ZrO_2$, $CeO_2$, $Nb_2O_5$, and/or $Al_2O_3$. Examples of aluminosilicates include materials like zeolites and/or clays. A solid support may have a total surface area between about 600 $m^2/g$ and about 1500 $m^2/g$. The first metal 120 deposited on a surface of the solid support 110 may include at least one of ruthenium, platinum, and/or palladium. The second metal 130 deposited on a surface of the solid support 110 may include at least one of tin, rhenium, cobalt, molybdenum, and/or tungsten. At least one of the first metal 120 and/or the second metal 130 may be deposited on an outer surface of the solid support 110 and/or on an internal surface of the solid support 110 (e.g. within internal pores and/or channels). A catalyst 100 having a first metal 120 and a second metal 130 deposited on a surface of a solid support 110 may have a range of particle diameters including powders (<100 micron), granules (100 micron to 1 mm), and pellets (>1 mm).

Figure 2:
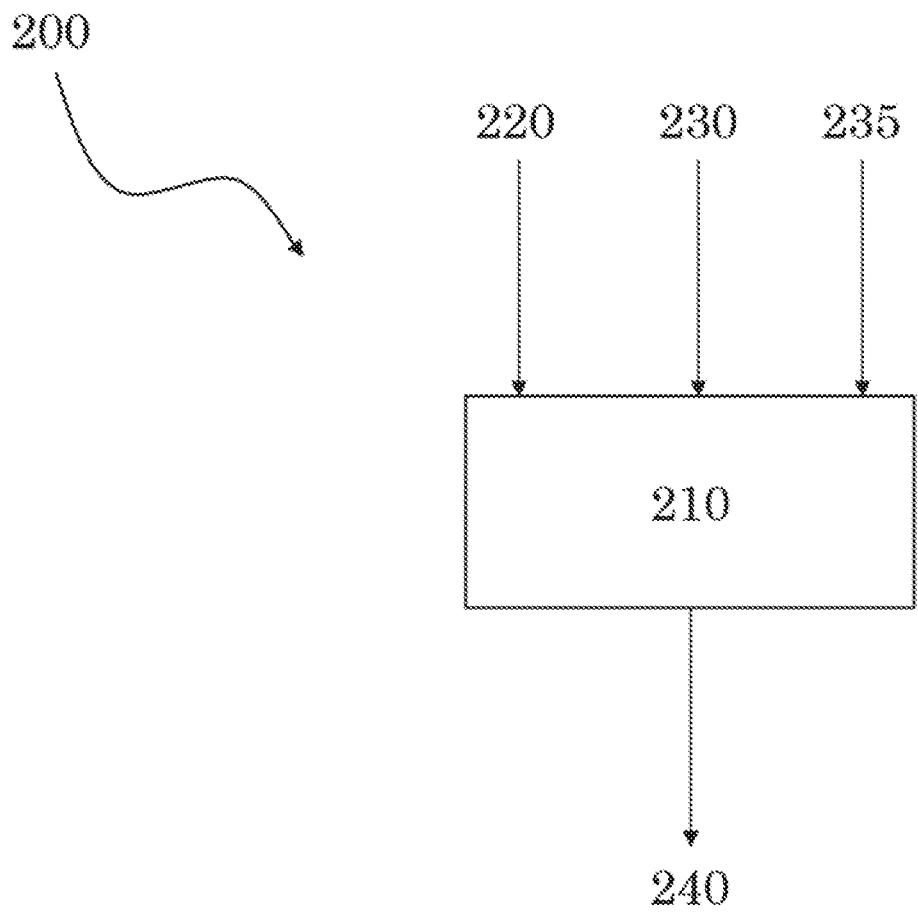
FIG. 2 illustrates a method for contacting a carboxylic acid and hydrogen with a catalyst to form an alcohol, according to some embodiments of the present disclosure.

FIG. 2 illustrates a method 200 for producing an alcohol 240, where the method includes contacting 210 a carboxylic acid 230 and hydrogen ($H_2$) 220 with a catalyst 235 as described above. In some embodiments of the present disclosure, the contacting 210 may include providing the hydrogen 220 to a slurry that includes the carboxylic acid 230 in a liquid phase, mixed with the catalyst 235 that includes a first metal and a second metal, both deposited on a solid support. Such a slurry may be contained within a batch stirred-tank reactor and/or a continuous stirred-tank reactor. In some embodiments of the present disclosure, the catalyst 235 may be positioned within a packed-bed reactor and the carboxylic acid 230 and the hydrogen 220 may be directed through the packed-bed reactor such that the carboxylic acid 230 and the hydrogen 220 contact the catalyst and react to form the alcohol 240. Thus, in some embodiments, the hydrogen 220 may be present in a gas phase and/or in a liquid phase. The flow of the hydrogen 220 may be either counter-current or co-current to the flow of the carboxylic acid 230.

Figure 3A:
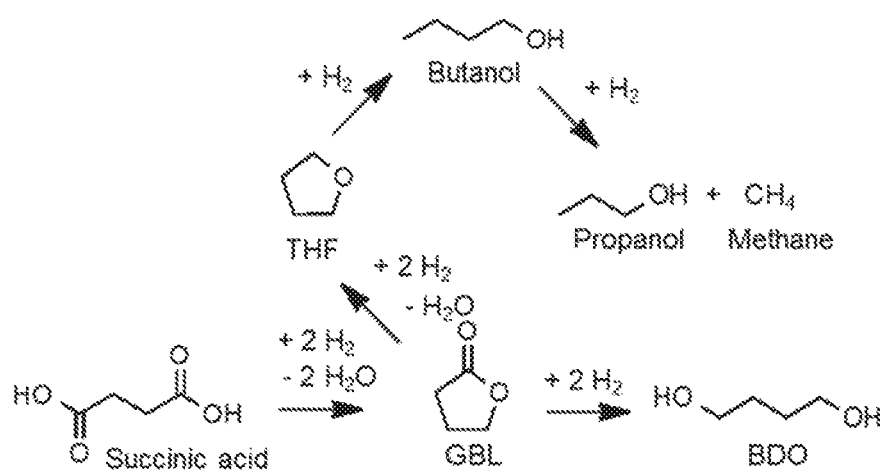
FIG. 3A illustrates an example of a reaction scheme of the reduction of succinic acid to 1,4-butanediol, according to one embodiment of the present disclosure.
Figure 3B:
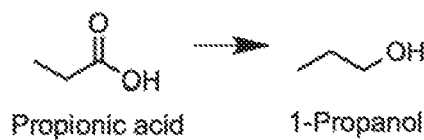
FIG. 3B illustrates an example of a reaction scheme of the reduction of propionic acid to 1-propanol, according to one embodiment of the present disclosure.
Figure 3C:
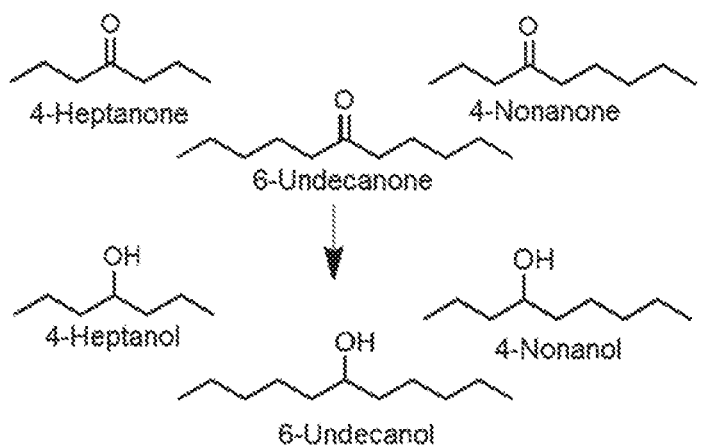
FIG. 3C illustrates an example of a reaction scheme of the reduction of various ketones to alcohols, according to one embodiment of the present disclosure.

FIGS. 3A-3C illustrate three examples of reaction schemes according to some embodiments of the present disclosure, FIG. 3A for converting succinic acid (a carboxylic acid) and hydrogen to BDO (an alcohol), through an intermediate γ-butyrolactone (GBL), FIG. 3B for converting propionic acid to 1-propanol, and FIG. 3C for converting various ketones to alcohols, where the reactions are catalyzed by bimetallic, solid-supported catalysts (as shown in FIG. 1).

Catalyst Synthesis and Characterization:

For succinic acid hydrogenation reactions, monometallic and bimetallic catalysts were initially synthesized on Darco powder activated carbon (PAC) for batch reactor screening and granular activated carbon (GAC) for packed-bed reactions. Prior to metal loading, the powder support was sieved to <270 mesh (53 micron) and the granular pellets (30-50 mesh; 300-600 micron) were used as received. The native AC support displayed a point of zero charge of pH 7.7, which was lowered to a 3.5 by nitric acid treatment. The supports were treated with concentrated nitric acid for 12-24 hours, washed with DI water until a neutral solution pH was reached, and dried under nitrogen. The PGMs, Ru, Pt, and Pd, were loaded onto the acidified AC support via strong electrostatic adsorption (SEA) using the following cationic precursors: hexmine ruthenium(III) chloride for Ru, tetraamineplatinum(II) nitrate for Pt, and tetraaminepalladium(II) chloride monohydrate for Pd. The SEA method used is as follows: the AC support was put into high pH aqueous solutions of ammonium hydroxide to deprotonate the AC surface. The primary metal precursors were added to the AC solution and stirred at room temperature for 2-4 hours. The material was then filtered, dried, and reduced in 200 sccm of pure $H_2$ for 4 hours at 450° C. These steps were repeated using the filtrate from the first step until the desired metal loading was achieved. Secondary oxophilic metals, Re and Sn, were loaded onto the monometallic catalysts via incipient wetness impregnation (IWI), using tin(II) chloride dissolved in acetone for Sn and ammonium perrhenate dissolved in DI water for Re. After the desired metal loadings were achieved, catalysts were dried and reduced in 200 sccm of pure $H_2$ at 450° C. for at least 2 hours.

For the related results and figures, the catalysts denoted as "metal"/PAC (e.g. Ru/PAC or Ru—Sn/PAC) refer to catalysts on the powder support at an approximate loading of 4 wt % of the primary metal, whereas catalysts denoted as "metal"/GAC refer to catalysts on the granular support at an approximate loading of 4 wt % of the primary metal.

TABLE 1

Dispersion of fresh monometallic catalysts supported on PAC used in batch screening reactions for succinic acid reduction to BDO.

| Catalyst | $H_2$ uptake (μmol $g^{-1}$) | Dispersion (%) | Particle dia. (nm) |
| --- | --- | --- | --- |
| 5.2% Pt/PAC | 86.2[a] | 35 | 1.9 |
| 4.6% Pd/PAC | 82.2[b] | 25 | 4.4 |
| 4.3% Ru/PAC | 47.5[c] | 19 | 5.8 |

[a]Pt measured by $H_2$ pulse;
[b]Pd measured by $H_2$—$O_2$ pulse;
[c]Ru measured by $H_2$ TPD.

For propionic acid hydrogenation reactions, catalysts were supported onto Darco AC powder (PAC) and granular supports (GAC). Prior to metal loading, the powder support was sieved to <270 mesh (53 micron) loading and the granular pellets (30-50 mesh; 300-600 micron) were used as received. The native AC support displayed a point of zero charge of pH 7.7, which was lowered to a 3.5 by nitric acid treatment. The supports were treated with concentrated nitric acid for 12-24 hours, washed with DI water until a neutral solution pH was reached, and dried under nitrogen. The PGMs, Ru, Pt, and Pd, were loaded onto the acidified AC support via SEA using the following cationic precursors: hexmine ruthenium(III) chloride for Ru, tetraamineplatinum(II) nitrate for Pt, and tetraaminepalladium(II) chloride monohydrate for Pd. The SEA method used is as follows: the AC support was put into high pH aqueous solutions of ammonium hydroxide to deprotonate the AC surface. The primary metal precursors were added to the AC solution and stirred at room temperature for 2-4 hours. The material was then filtered, dried, and reduced in 200 sccm of pure $H_2$ for 4 hours at 450° C. These steps were repeated using the filtrate from the first step until the desired metal loading was achieved. Secondary oxophilic metals, Re and Sn, were loaded onto the monometallic catalysts via IWI, using tin(II) chloride dissolved in acetone for Sn and ammonium perrhenate dissolved in DI water for Re. After the desired metal loadings were achieved, catalysts were dried and reduced in 200 sccm of pure $H_2$ at 450° C. for at least 2 hours.

For the related results and figures, the catalysts denoted as "metal"/PAC (e.g. Ru/PAC or Ru—Sn/PAC) refer to catalysts on the powder support at an approximate loading of 4 wt % of the primary metal, whereas catalysts denoted as "metal"/GAC refer to catalysts on the granular support at an approximate loading of 4 wt % of the primary metal.

Figures 4A, 4B, 4C:
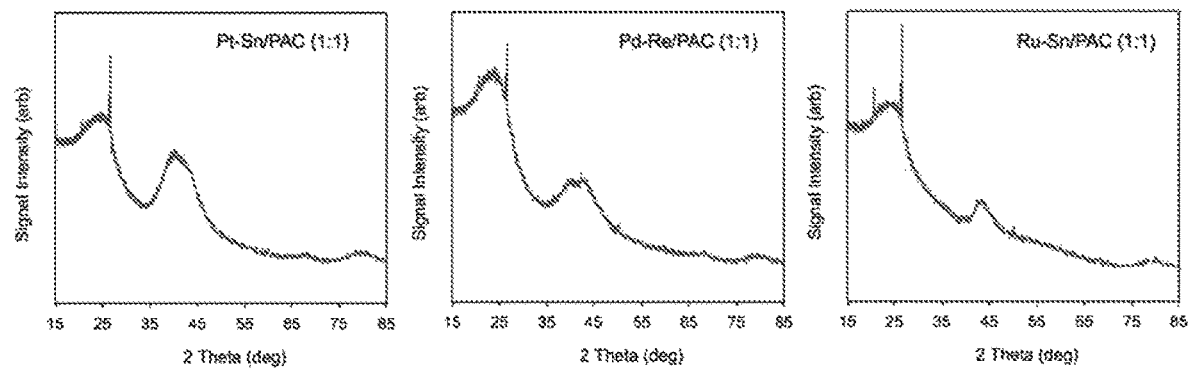
FIG. 4A illustrates XRD characterization data of fresh Pt—Sn/PAC (1.0:1.0) bimetallic powder catalysts used in a batch reactor screening, according to some embodiments of the present disclosure.
FIG. 4B illustrates XRD characterization data of fresh Pd—Re/PAC (1.0:1.0) bimetallic powder catalysts used in a batch reactor screening study, according to some embodiments of the present disclosure.
FIG. 4C illustrates XRD characterization data of fresh Ru—Sn/PAC (1.0:1.0) bimetallic powder catalysts used in a batch reactor screening, according to some embodiments of the present disclosure.

Detailed characterization described herein was performed on the powder bimetallic catalysts with a nominal 1.0:1.0 weight ratio, where all primary metal loadings are nominally 4 wt %. Bulk elemental analysis by inductively coupled plasma mass spectroscopy (ICP-MS) showed metal mass ratios comparable to nominal values, while X-ray photoelectron spectroscopy (XPS) showed predominant surface enrichment of the oxophilic secondary metal, consistent with the sequential loading technique, as shown in Table 2, below. X-ray diffraction (XRD) analysis showed broad peaks in the respective loaded metal regions of interest (see FIGS. 4A-4C), supportive of highly disperse metal crystallites. Likewise, elemental mapping by scanning electron microscopy—energy dispersive x-ray spectroscopy (SEM-EDS) showed evenly distributed metals across the particles, and transmission electron microscopy (TEM) imaging confirmed crystallites<5 nm in diameter (see FIGS. 5A-L). Chemisorption of the Pd—Re/PAC catalyst showed significant $H_2$ uptake (456 micromol $g^{-1}$), while the Ru—Sn/PAC and Pt—Sn/PAC catalysts were extremely low (<5 micromol $g^{-1}$) (see Table 2 below). Further testing of Ru—Sn/PAC by CO pulse chemisorption also showed muted uptake (5.9 micromol $g^{-1}$), suggestive of a predominantly Sn surface. Lastly, nitrogen physisorption confirmed comparable activated carbon support surface areas (773-888 $m^2$ $g^{-1}$), with a narrow range of pore volumes (0.43-0.51 $cm^3$ $g^{-1}$) and pore diameters (14.2-14.6 Å) (see Table 2 below).

Lewis acid sites (1445 $cm^{-1}$) and free or H-bonded pyridine (1590 $cm^{-1}$). Typically, Lewis acidity on Sn-based catalysts is assigned to Sn(IV) sites on the catalyst surface, suggesting that the Ru—Sn/PAC catalyst contains $SnO_2$ domains, even after reduction and without air exposure.

Figure 6A:
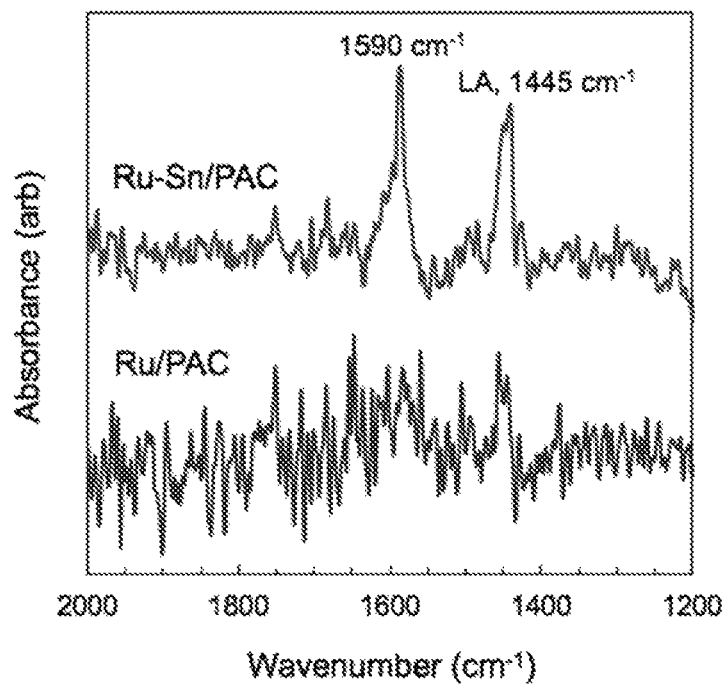
FIGS. 6A and 6B illustrate DRIFTS and TPR characterization data, respectively, of the Ru—Sn/PAC (1.0:1.0) and Ru/PAC powder catalysts, according to some embodiments of the present disclosure.
Figure 6B:
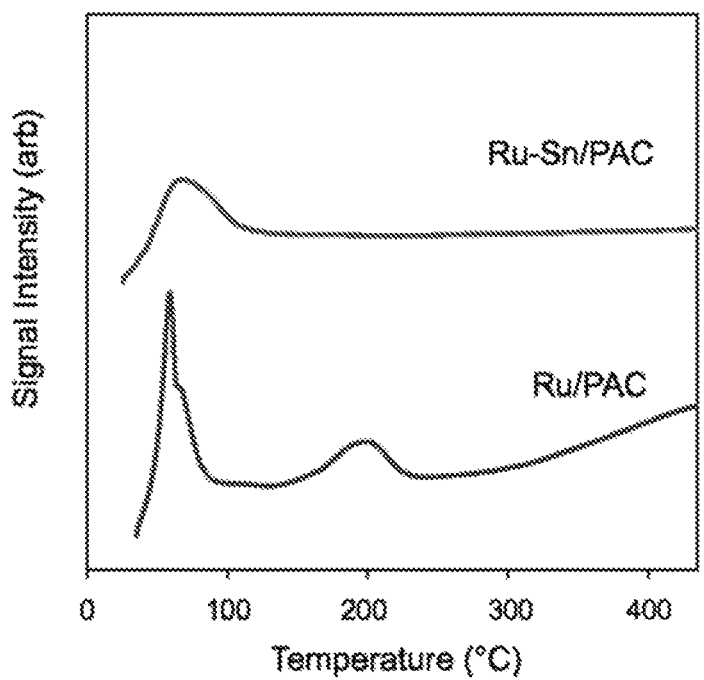
Figure 7:
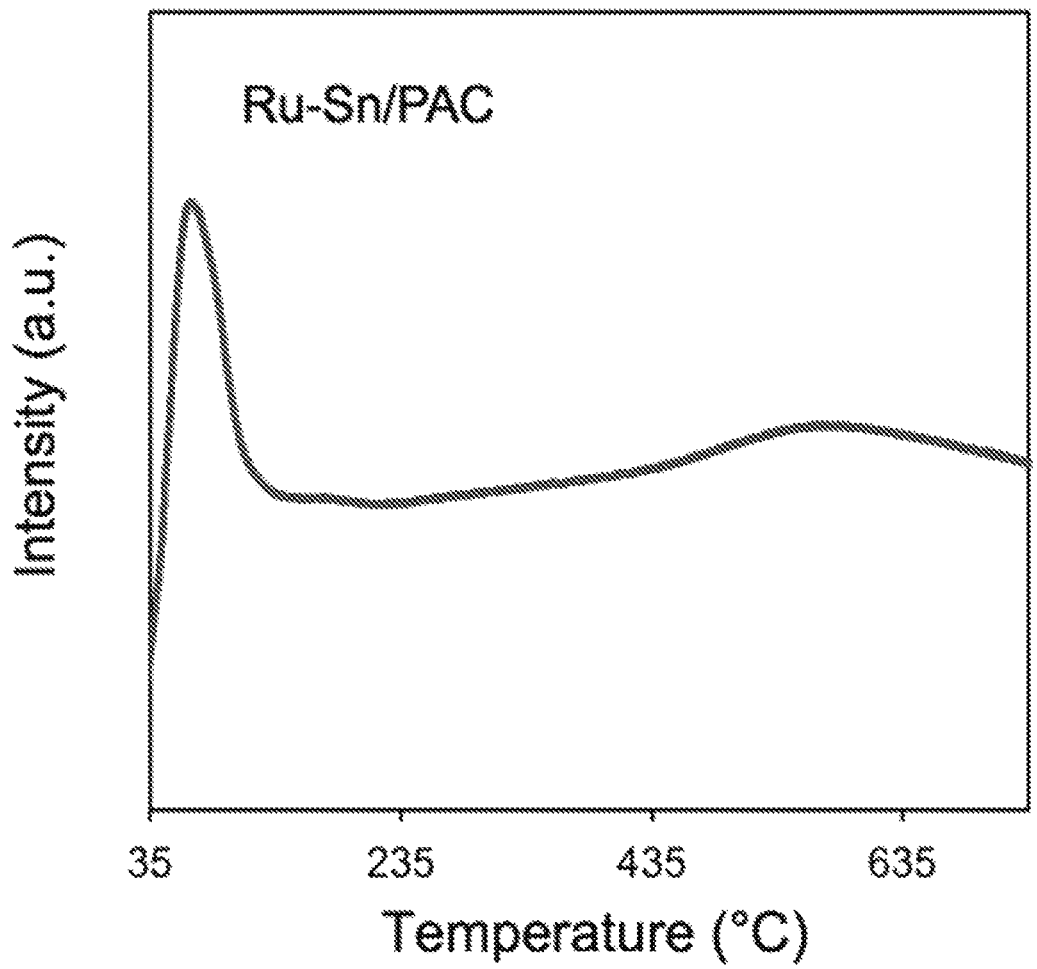
FIG. 7 illustrates a high temperature TPR characterization data of Ru—Sn/PAC (1.0:1.0), according to some embodiments of the present disclosure. The early onset peak (<100° C.) was attributed to the reduction of surface Ru, while the late onset peak (>400° C.) was attributed to the evolution of CO and $CO_2$ from the nitric acid-treated activated carbon support.

Temperature-programmed reduction (TPR) profiles further highlighted the influence of Sn on catalyst behavior (see FIG. 6B). The monometallic Ru/PAC catalyst showed a low temperature peak between 60-80° C., suggestive of amorphous $RuO_2$ reduction, as well as a smaller reduction peak between 180-220° C., suggestive of bulk $RuO_2$ reduction. At temperatures above 250° C., the onset of a broad peak is observed that is suggestive of CO and $CO_2$ evolution from oxygen functional groups on the nitric acid-treated activated carbon support. For the Ru—Sn/PAC (1.0:1.0) catalyst, a low temperature reduction peak during TPR was observed between 50-100° C., although $H_2$ chemisorption showed only 9% of the $H_2$ uptake when compared to monometallic Ru/PAC (see Tables 1 and 2 above). In comparison to other Ru—Sn bimetallic systems, reduction peaks were not observed between 250-350° C., suggesting weak interaction between Ru and Sn. At high temperatures above 400° C., a broad low magnitude peak was observed (see FIG. 7), potentially due to the reduction of oxygenated functional groups on the support or reduction of $SnO_2$.

Figure 8A:
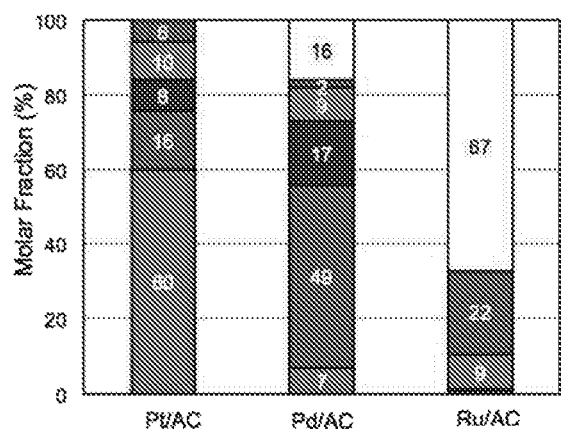
FIGS. 8A-8D illustrate data from monometallic and bimetallic powder catalyst batch reactor screening studies for the reduction of succinic acid to 1,4-BDO, according to some embodiments of the present disclosure.

Batch Reactor Screening:

Batch reactor screening experiments evaluated the activity and selectivity of monometallic and bimetallic powder catalysts for succinic acid reduction to BDO, with results reported on a molar yield basis. Overall, monometallic catalysts performed poorly when targeting BDO, as illustrated in FIG. 8A. For Pt/PAC, low activity for succinic acid reduction was observed with significant amounts of succinic acid remaining (60%) after 6 hours of reaction. For Pd/PAC, γ-butyrolactone (GBL) was the major product (66%). For Ru/PAC, molar losses were significant (67%), likely due to cracking reactions that formed light hydrocarbons. Significant non-target products were also observed (22%), consisting of propionic acid, propanol, and butanol.

TABLE 2

Properties of fresh powder bimetallic catalysts used in batch screening reactions for succinic acid reduction to BDO.

| Catalyst (~wt. ratio) | ICP (wt. %) | ICP (molar ratio) | XPS (molar ratio) | $H_2$ uptake (μmol $g^{-1}$) | $S_{BET}$ ($m^2$ $g^{-1}$) | Pore vol.$^a$ ($cm^3$ $g^{-1}$) | Pore dia.$^a$ (Å) |
|---|---|---|---|---|---|---|---|
| Ru—Sn/PAC (1:1) | 4.8% Ru 4.1% Sn | Ru to Sn 1.38 | Ru to Sn 0.41 | 4.3$^b$ | 773 | 0.51 | 14.2 |
| Pt—Sn/PAC (1:1) | 5.1% Pt 3.9% Sn | Pt to Sn 0.80 | Pt to Sn 0.51 | 0.3$^b$ | 794 | 0.43 | 14.4 |
| Pd—Re/PAC (1:1) | 4.5% Pd 3.7% Re | Pd to Re 1.22 | Pd to Re 1.63 | 456$^c$ | 888 | 0.44 | 14.6 |

$^a$Pore volume and average micropore diameter determined by BJH adsorption.
$^b$Measured by $H_2$ TPD.
$^c$Measured by $H_2$—$O_2$ titration.

Figure 8B:
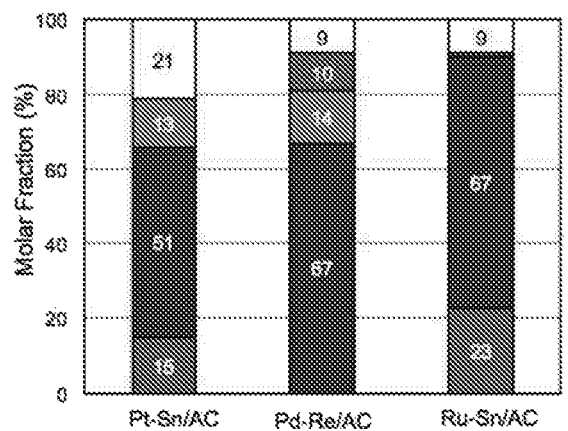

Further characterization was conducted to evaluate the impact of Sn on surface acidity and temperature dependent reducibility. Qualitative acidity measurements were performed using pyridine adsorption diffuse reflectance infrared Fourier-transform spectroscopy (DRIFTS), as shown in FIG. 6A. The monometallic Ru/PAC catalyst showed no adsorption of pyridine after flowing $N_2$ at 50° C. to purge the DRIFTS cell, consistent with the fully reduced metal and no pyridine adsorption on the catalyst support; however, the bimetallic Ru—Sn/PAC catalyst showed small yet distinct absorption bands at 1445 $cm^{-1}$ and 1590 $cm^{-1}$, indicative of Addition of an oxophilic secondary metal (e.g., Sn, Re) at a nominal 1.0:1.0 metal weight ratio dramatically improved the catalyst performance for selectivity towards BDO, as shown in FIG. 8B. Complete conversion of succinic acid was observed for all 1.0:1.0 powder bimetallic catalysts, with BDO as the primary product. BDO molar yields increased in the order of Pt—Sn/PAC (51%), Pd—Re/PAC (67%), and Ru—Sn/PAC (67%). For Pt—Sn/PAC, GBL (15%) and tetrahydrofuran (THF) (13%) were the major secondary products, with GBL serving as an intermediate to BDO. For Pd—Re/PAC, THF (14%) was a major secondary product. For Ru—Sn/PAC, GBL (23%) was the major secondary product, with negligible amounts of THF and non-target products.

Figure 8C:
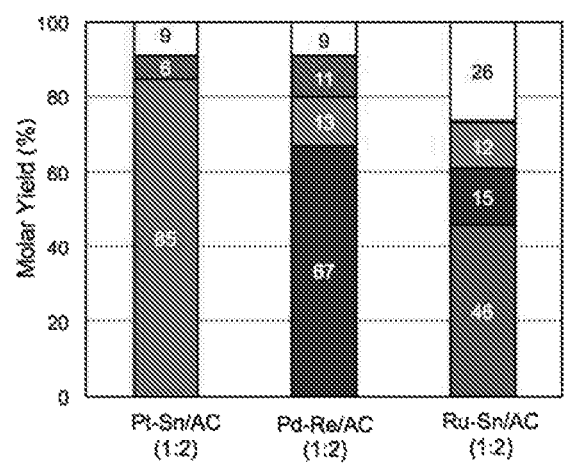
Figure 8D:
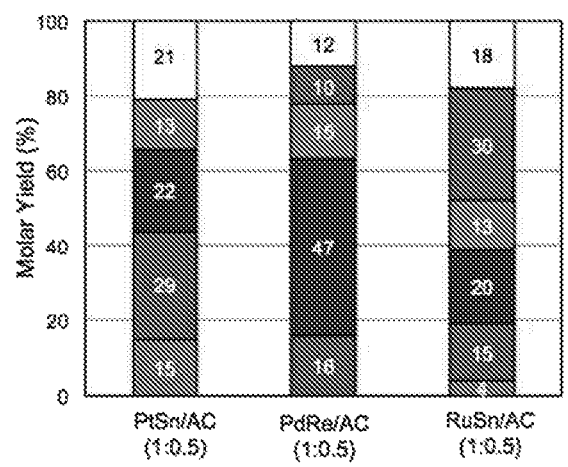

Further alterations to the bimetallic ratio did not result in significant gains in BDO yield, as shown in FIG. 8C and FIG. 8D. Increasing the secondary metal loading greatly reduced the activity of Pt—Sn/PAC (1.0:2.0), resulting in significant amounts remaining of succinic acid (85%). Likewise, Ru—Sn/PAC (1.0:2.0) showed less BDO and more of the intermediate GBL (46%), albeit with greater product losses and THF formation. Interestingly, increasing the Re loading of Pd—Re/PAC resulted in comparable product yields at the 1.0:2.0 and 1.0:1.0 metal weight ratios. Decreasing the secondary metal loading resulted in a less dramatic reduction in activity of Pt—Sn/PAC (1.0:0.5) with a comparable product distribution to the 1.0:1.0 metal ratio. For Ru—Sn/PAC, lower Sn loading (1.0:0.5) resulted in greater non-target products (30% sum of butanol, propanol, propionic acid), losses to lights (18%), and THF (13%), suggesting that sufficient mediation from Sn is a key requirement. Lastly, a lower Re loading with Pd—Re/PAC (1.0:0.5) moderately reduced the yield of BDO (47%) and resulted in a build-up of GBL (16%).

Figure 9A:
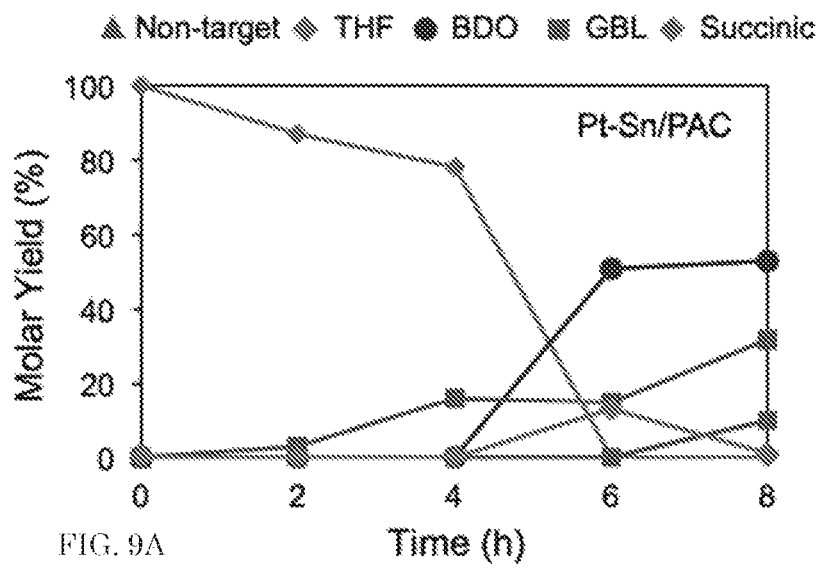
FIGS. 9A-9C illustrate data from bimetallic powder catalysts batch reaction time screening studies, according to some embodiments of the present disclosure.
Figure 9B:
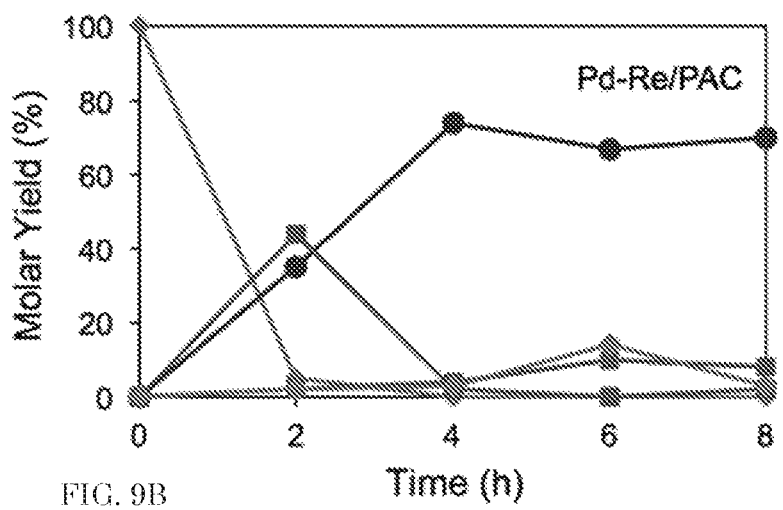
Figure 9C:
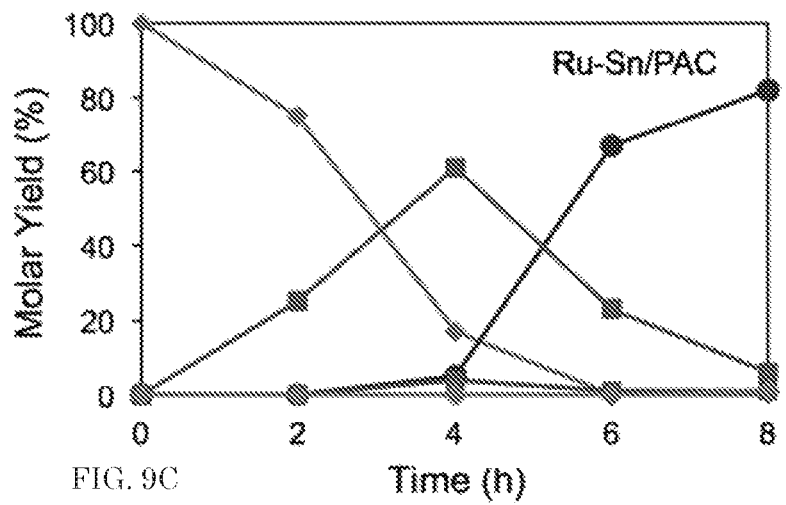

Batch reactor time series experiments using powder bimetallic catalysts with a 1.0:1.0 metal ratio demonstrated the progression of product selectivity to BDO, as shown in FIGS. 9A-9C. For Pt—Sn/PAC, succinic acid conversion was low at 2 hours, requiring 6 hours for complete conversion. Maximum BDO selectivity was observed at 8 hours, with a molar yield of 53% (see FIG. 9A). For Pd—Re/PAC, succinic acid conversion was nearly complete after 2 hours, with GBL as the primary product. By 4 hours, maximum BDO selectivity was observed with a molar yield of 74% (see FIG. 9B). Lastly, Ru—Sn/PAC displayed moderate activity for succinic acid reduction with 25% conversion after 2 hours and required 6 hours for complete conversion. By 8 hours, residual GBL was converted into BDO, resulting in a BDO molar yield of 82% (see FIG. 9C). For both Ru—Sn/PAC and Pt—Sn/PAC catalysts, an inhibition period was observed during the first 4 hours. This lag phase could potentially be attributed to several factors, including catalyst reduction after air exposure, restructuring under working conditions, or oxidation of the catalyst surface when interacting with the organic substrate.

Post-reaction characterization of the Ru—Sn/PAC (1.0:1.0) catalyst confirmed stable material properties after batch screening reactions. ICP analysis was unable to detect Ru or Sn in the filtered liquid phase, confirming the stability of the catalyst against leaching. In comparison, leaching analysis of a monometallic Sn/PAC catalyst under the same conditions resulted in 13.95 ppm of Sn, suggesting Ru mitigates Sn leaching during succinic acid hydrogenation. SEM-EDS mapping of the catalyst confirmed that Ru and Sn remained uniformly dispersed on the catalyst support (see FIGS. 10A-10C), and TEM imaging showed metal crystallites<5 nm in diameter (see FIG. 10D). These results were consistent with the broad peaks observed by XRD for the fresh and spent catalyst (see FIG. 10E and FIG. 10F).

Figure 11A:
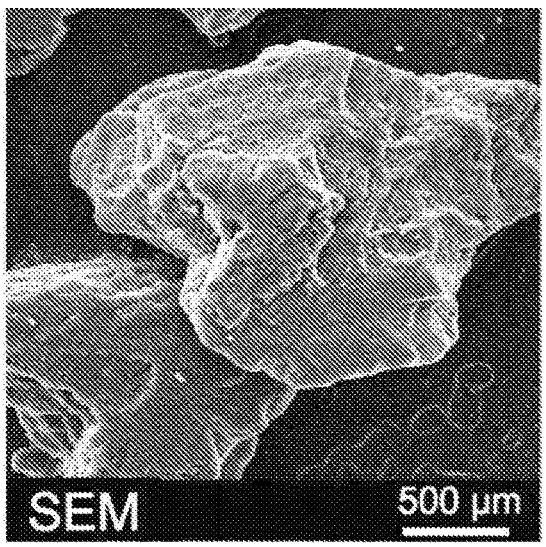
FIGS. 11A-11D illustrate SEM-EDS (FIGS. 11A-11C) and TEM (FIG. 11D) characterization data of fresh Ru—Sn/GAC (1.0:1.0) catalyst for use in a trickle-bed reactor, according to some embodiments of the present disclosure.
Figure 11B:
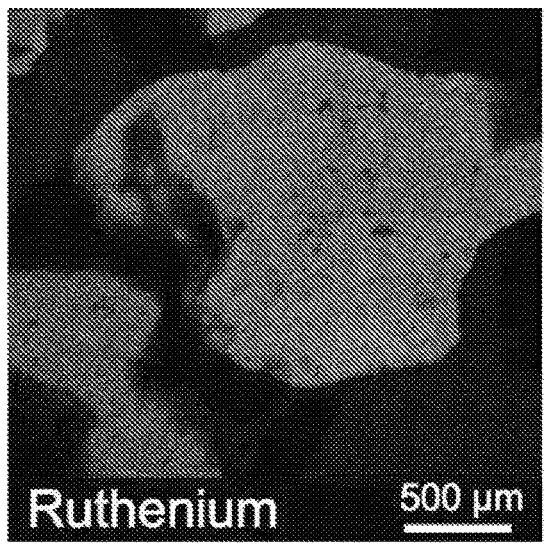
Figure 11C:
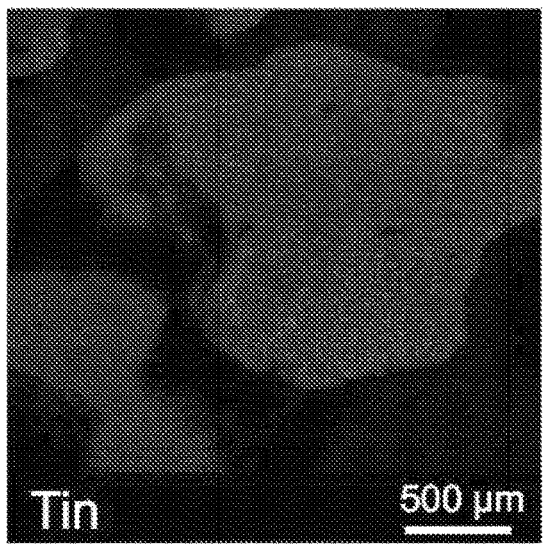
Figure 11D:
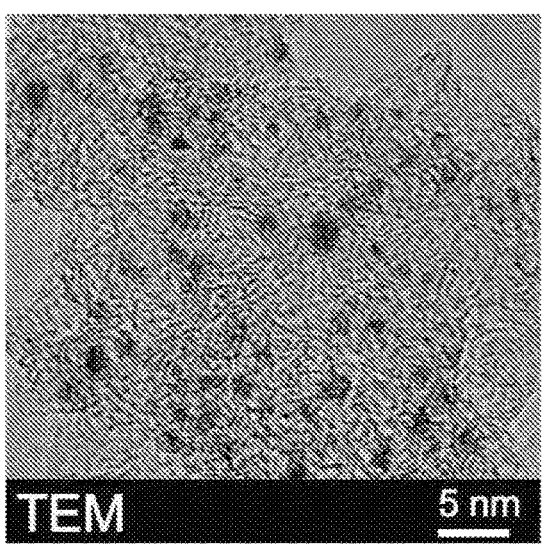

Ru—Sn Trickle-Bed Reactor Testing:

Based on the favorable batch reactor results, the Ru—Sn (1.0:1.0) catalyst was synthesized on granular activated carbon (GAC) for trickle-bed reactor testing. The granular catalyst synthesis procedure was identical to the powder catalyst, with the exception of using granular Darco activated carbon sieved to 30-50 mesh to minimize pressure drop across the reactor bed. SEM-EDS mapping of the fresh granular catalyst confirmed an even distribution of Ru and Sn across the support (see FIGS. 11A-11C), and TEM imaging showed disperse metal crystallites<5 nm in diameter (see FIG. 11D). Chemisorption showed poor $H_2$ uptake (3.2 micromol g$^{-1}$; see Table 3 below), similar to the powder catalyst used in the batch reactor screening study (see Table 2 above). Lastly, nitrogen physisorption determined that the granular catalyst had a lower surface area (652 m$^2$ g$^{-1}$) compared to the powder (773 m$^2$ g$^{-1}$) support, and a comparable pore volume (0.45 cm$^3$ g$^{-1}$) and pore diameter (14.4 Å) (see Table 3).

TABLE 3

Properties of the fresh and spent Ru—Sn/GAC (1.0:1.0) catalyst used for the complete conversion of succinic acid in the silica-coated trickle-bed reactor tube. Reaction conditions were as follows: 5 wt. % succinic acid in water, liquid flow rate 0.10 mL min$^{-1}$, temperature 170° C., 124 bar $H_2$ flowing at 200 sccm, catalyst loading 5 g.

| Catalyst (~wt. ratio) | ICP (wt. %) | ICP (molar ratio) | XPS (molar ratio) | $H_2$ uptake (μmol g$^{-1}$) | $S_{BET}$ (m$^2$ g$^{-1}$) | Pore vol.[a] (cm$^3$ g$^{-1}$) | Pore dia.[a] (Å) |
|---|---|---|---|---|---|---|---|
| Fresh Ru—Sn/GAC (1:1) | 4.1% Ru 4.0% Sn | Ru to Sn 1.21 | Ru to Sn 0.46 | 3.2 | 652 | 0.45 | 14.4 |
| Spent Ru—Sn/GAC (1:1) | 4.0% Ru 3.8% Sn | Ru to Sn 1.26 | Ru to Sn 0.15 | 2.4 | 595 | 0.49 | 9.8 |

[a]Pore volume and average micropore diameter determined by BJH adsorption.

Figure 12:
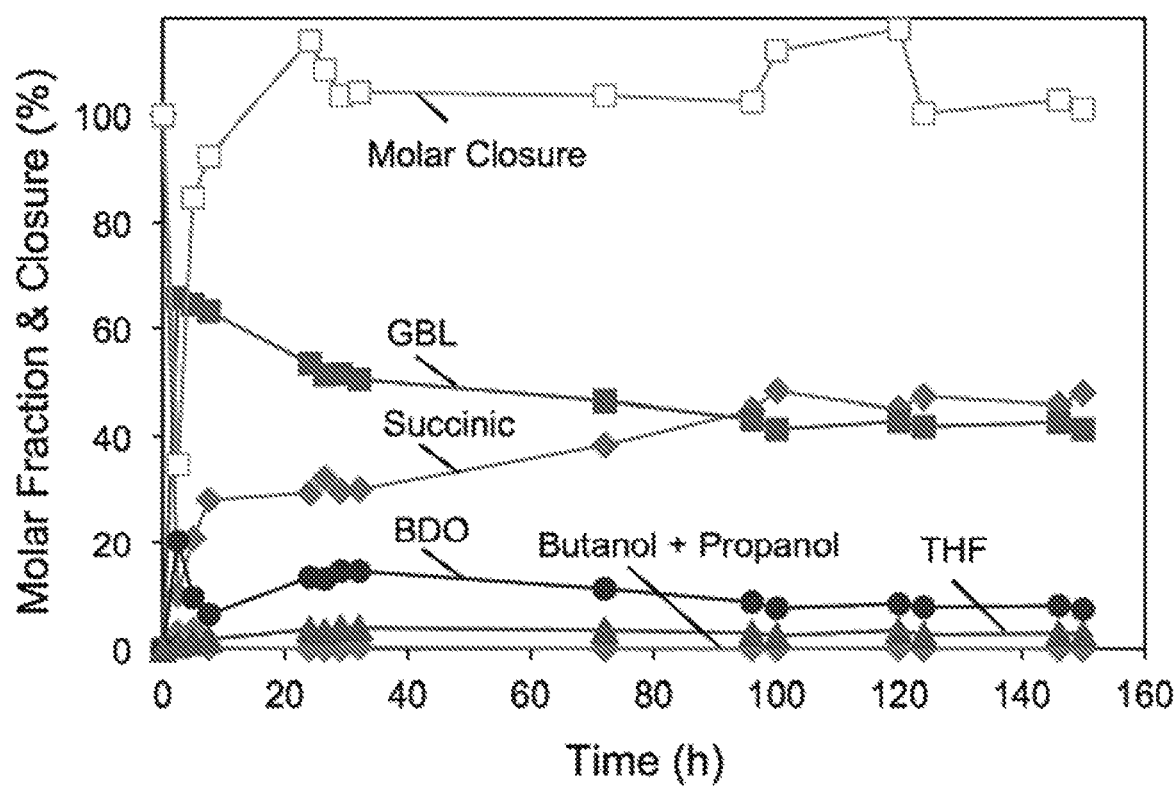
FIG. 12 illustrates trickle-bed reactor performance data using an uncoated stainless steel reactor tube for the partial conversion (<25% molar) of succinic acid using Ru—Sn/GAC (1.0:1.0), according to some embodiments of the present disclosure.
Figure 13A:
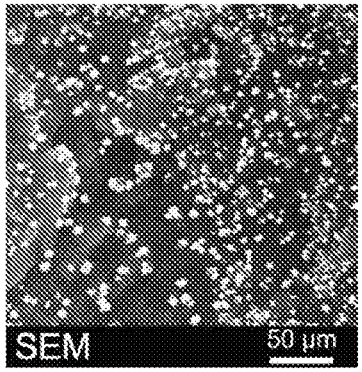
FIGS. 13A-13F illustrate characterization data by SEM-EDS of the spent Ru—Sn/GAC (1.0:1.0) catalyst used in the uncoated trickle-bed reactor tube for 150 hours of time-on-stream succinic acid hydrogenation under partial conversion (<25% molar) conditions, according to some embodiments of the present disclosure.
Figure 13B:
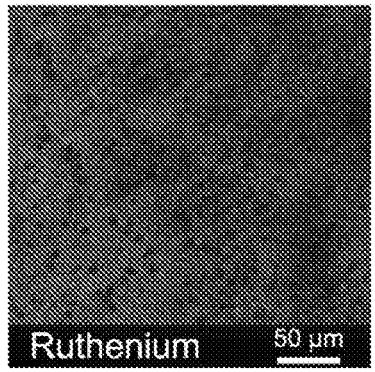
Figure 13C:
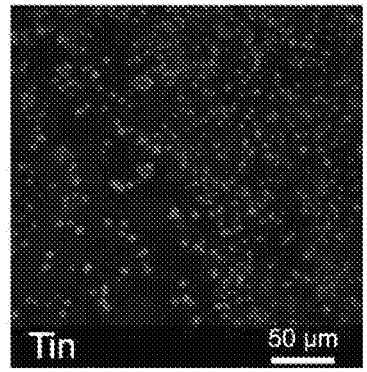
Figure 13D:
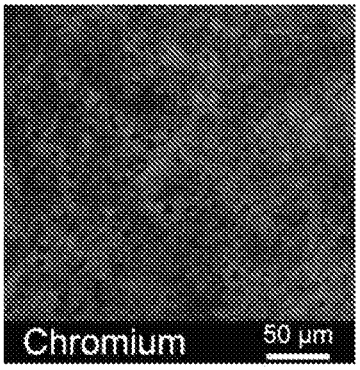
Figure 13E:
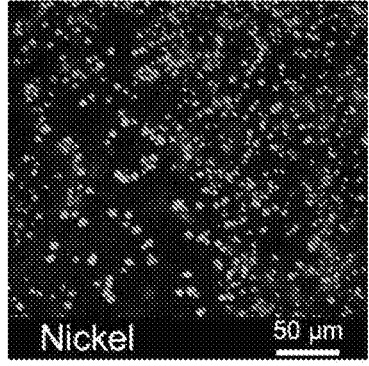
Figure 13F:
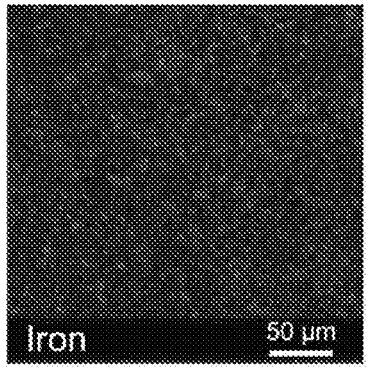
Figure 14A:
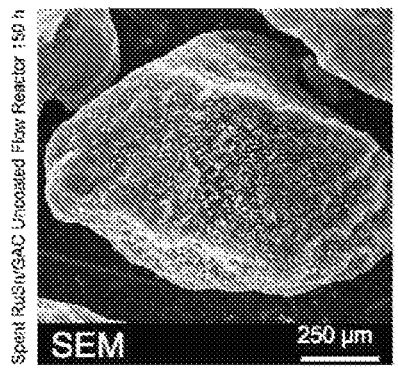
FIGS. 14A-14I illustrate SEM-EDS (FIGS. 14A-14F) and TEM (FIGS. 14G-14I) characterization data of the spent Ru—Sn/GAC (1.0:1.0) catalyst used in the uncoated stainless steel reactor tube for 150 hours of time-on-stream succinic acid hydrogenation under partial conversion (<25% molar) conditions, according to some embodiments of the present disclosure.
Figure 14B:
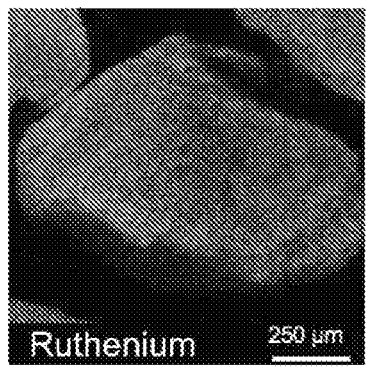
Figure 14C:
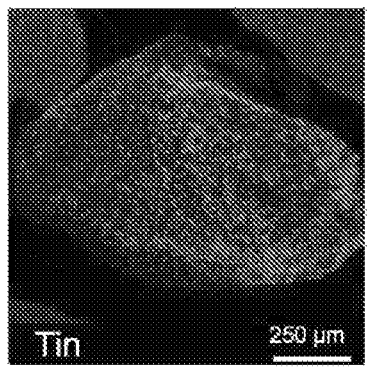
Figure 14D:
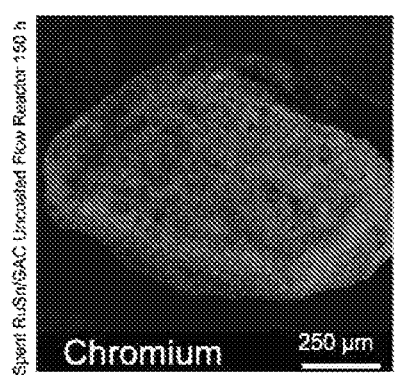
Figure 14E:
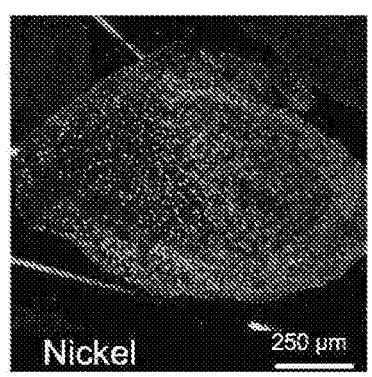
Figure 14F:
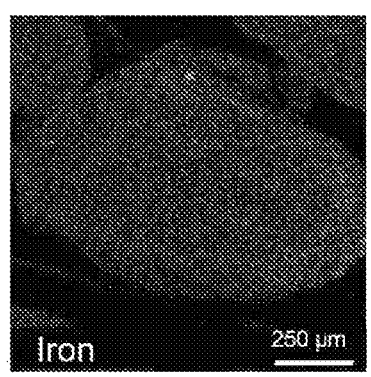
Figure 14G:
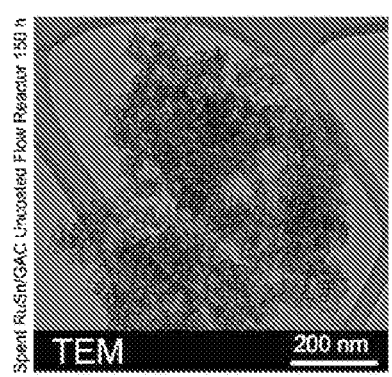
Figure 14H:
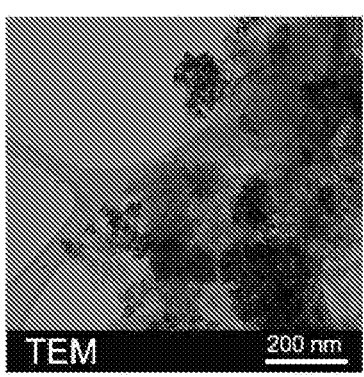
Figure 14I:
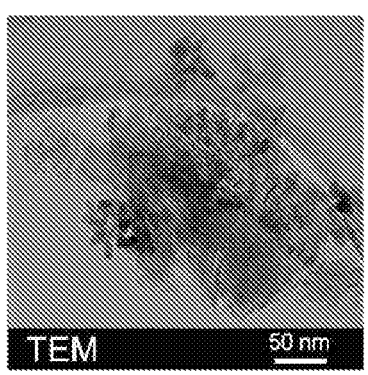

Initial trickle-bed reactor experiments were performed with the Ru—Sn/GAC (1.0:1.0) catalyst using an uncoated 316 stainless steel reactor tube. Partial conversion (<25% molar) runs showed a steady decline in catalyst activity over 100 hours prior to achieving steady state performance (see FIG. 12). Post-reaction characterization of the catalyst confirmed that significant compositional and structural changes had occurred. SEM-EDS imaging and mapping of the catalyst (see FIGS. 13A-13F and FIGS. 14A-14I) revealed the deposition of Cr and Ni on the surface, which likely leached from the stainless steel reactor tube. Further elemental mapping by SEM-EDS revealed that, although Ru, Cr, and Fe were evenly distributed, discrete Ni—Sn crystallites had formed (see FIGS. 13A-13F). The formation of Ni—Sn crystallites suggests preferential alloying. Previous efforts have shown Ni—Sn to be active for hydrogenation reactions with glucose, which may account for the continued hydrogenation activity with succinic acid despite catalyst metal crystallite restructuring. TEM imaging of the catalyst confirmed a heterogeneous distribution of dispersed and sintered metal crystallites (see FIGS. 14G-14I), consistent with the SEM-EDS elemental mapping. ICP analysis of the spent catalyst confirmed significant levels of Cr (2.8%) and Ni (1.7%) relative to the fresh catalyst (Cr 13 ppm; Ni 18 ppm), and comparable levels of Fe (2080 ppm fresh; 1920 ppm spent) native to the activated carbon support (see Table 4 below).

TABLE 4

ICP-MS elemental analysis of fresh and spent Ru—Sn/GAC (1.0:1.0) catalysts to evaluate the impact of stainless steel leaching.

| Elemental Composition | Fresh Ru—Sn/GAC (1:1) | Spent Ru—Sn/GAC Uncoated Tube | Spent Ru—Sn/GAC Coated Tube |
|---|---|---|---|
| Cr (ppm) | 13 | 28,000 | 4,250 |
| Ni (ppm) | 18 | 17,000 | 5,570 |
| Fe (ppm) | 2080 | 1,920 | 2,840 |

To address stainless steel leaching, the reactor tube was coated with silica by chemical vapor deposition (CVD). With the silica-coated reactor tube, no break-in lag period was observed and stable activity was achieved for 84 hours under partial conversion (<25% molar) conditions (see Table 5 below). ICP analysis of the reactor effluent showed no detectable leaching of Ru or Sn, and analysis of spent catalysts showed significantly decreased levels of Cr, Ni, and Fe compared to the spent catalyst that was tested in the uncoated reactor tube (see Table 4 above). As supported by the post-reaction catalyst characterization data below, these results suggest that restructuring of Ru—Sn can be prevented if stainless steel leaching is avoided, resulting in stable catalyst performance.

TABLE 5

Trickle-bed reactor performance for the partial conversion (<25% molar) of succinic acid with Ru—Sn/GAC (1.0:1.0) using a stainless steel reactor tube that was coated with silica by CVD. Reaction conversion conditions were as follows: succinic acid 5 wt. % in water, liquid flow rate 0.25 mL, min$^{-1}$, temperature 180° C., 124 bar H$_2$ flowing at 200 sccm, catalyst loading 200 mg.

| Time-on-stream (h) | Succinic (%) |
|---|---|
| 18 | 84.4 |
| 24 | 85.0 |
| 36 | 84.7 |
| 45 | 85.7 |
| 48 | 83.3 |
| 60 | 85.2 |
| 66 | 85.2 |
| 70 | 85.0 |
| 84 | 84.8 |

Figure 15A:
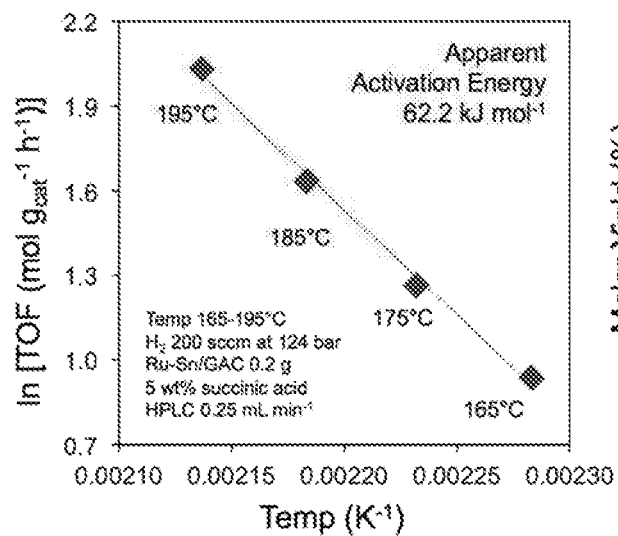
FIG. 15A illustrates the apparent activation energy for succinic acid hydrogenation under partial conversion conditions, according to some embodiments of the present disclosure.

After confirming stable catalyst behavior with the silica-coated reactor tube, further work was conducted to examine the apparent activation energy and prolonged stability under complete conversion conditions. Under partial conversion conditions (<25% molar conversion, 5 wt. % succinic acid, liquid flow rate 0.25 mL min$^{-1}$, temperature 180° C., 124 bar H$_2$ flowing at 200 sccm, catalyst loading 200 mg), an apparent activation energy of 62.2 kJ mol$^{-1}$ was observed for succinic acid reduction, as shown in FIG. 15A. Subsequent experiments under complete conversion conditions (5 wt. % succinic acid in water, liquid flow rate 0.1 mL min$^{-1}$, temperature 170° C., 124 bar H$_2$ flowing at 200 sccm, catalyst loading 5 g) confirmed stable catalyst performance for 96 hours of time-on-stream, with an average molar yield of 71% BDO, 15% THF, 3% GBL, and 2% butanol (see FIG. 15B). Trace propanol was also present at below 0.5% molar yield, resulting in an average liquid product molar closure of 91%.

Figures 16A, 16B:
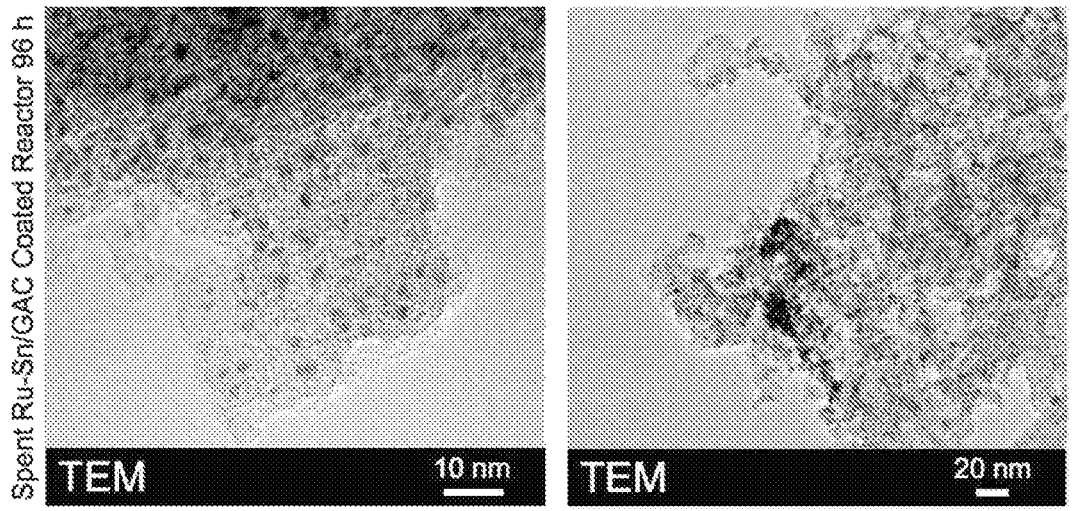
FIG. 16A illustrates TEM imaging data of spent Ru—Sn/GAC (1.0:1.0), according to some embodiments of the present disclosure.
FIG. 16B illustrates TEM imaging data of spent Ru—Sn/GAC (1.0:1.0), according to some embodiments of the present disclosure.

Characterization of the spent catalyst from the 96-hour complete conversion run in the silica-coated reactor tube showed minor material property changes compared to the catalysts used in the uncoated reactor tube. Bulk elemental analysis of the spent catalyst by ICP-MS confirmed significantly lower levels of Cr (4250 ppm) and Ni (5570 ppm) compared to runs in the uncoated reactor tube, suggesting that the silica coating dramatically reduces stainless steel leaching (see Table 4 above). Ru and Sn metal loadings were comparable to the fresh catalyst; however, XPS elemental analysis revealed a lower ratio of Ru to Sn, indicating further migration and enrichment of Sn on the surface of the catalyst under operating conditions (see Table 3 above). Nitrogen physisorption analysis of the activated carbon support showed a 9% reduction in surface area to 595 m$^2$ g$^{-1}$, 9% increase in pore volume to 0.49 cm$_3$ g$^{-1}$, and a 36% reduction in pore diameter to 9.8 Å (see Table 3 above). These results support a reduction in average pore size with prolonged exposure to reaction conditions, potentially due to support restructuring or oligomer fouling in larger pore diameters. TEM imaging of the spent catalyst revealed a non-uniform distribution of highly disperse metal crystallites, as well as small patches of agglomerated metal particles (see FIG. 16A and FIG. 16B). However, it was not determined if the agglomerated regions were due to Ru—Sn restructuring or the deposition of Ni, Cr, and Fe to form distinct crystallites.

Monometallic Vs. Bimetallic Catalysts:

As shown above, monometallic Ru/AC is highly active for converting succinic acid to THF, non-targets (butanol, propanol, propionic acid), and gas phase products, but poorly selective to BDO. Ru/AC alone resulted in complete conversion and significant cracking via hydrogenolysis of succinic acid under batch screening conditions employed in this work (180° C., 100 bar H$_2$). To target BDO, the addition of at least one secondary promoter metal may facilitate the subsequent reduction of GBL. The addition of Sn dramatically improved the selectivity of Ru/AC for BDO and muted hydrogenolysis activity. The sequential preparation method to load Sn on top of Ru resulted in surface enrichment of Sn, extremely low hydrogen affinity, slight Lewis acidity, and no discernable bimetallic reduction peaks by TPR (see Table 2). This suggests that Sn overcoats Ru as opposed to forming a distinct bimetallic alloy. It should be noted that bimetallic crystallite structures are highly influenced by the elemental composition, synthetic method, and reaction conditions, affording possibilities for tuning the surface reactivity for a given chemical pathway.

Ru—Sn/GAC Continuous-Flow Performance:

The importance of compatible reactor metallurgy was evident when processing succinic acid continuously in the trickle-bed reactor. The Ru—Sn crystallites dramatically restructured to form Ni—Sn crystallites when performing the reactions in an uncoated stainless reactor tube (see FIGS. 13A-13F), which resulted in a steady decline in catalyst performance (see FIG. 12). Coating the stainless steel reactor tube with silica by CVD greatly muted the deposition of Ni and Cr (Table 2) and minimized restructuring of Ru—Sn/GAC (see FIGS. 16A-16B). Alternative reactor metallurgies such as Hastelloy and titanium may be suitable for acidic aqueous process conditions, although their impact on flow reactor capital costs must be considered.

Figure 15B:
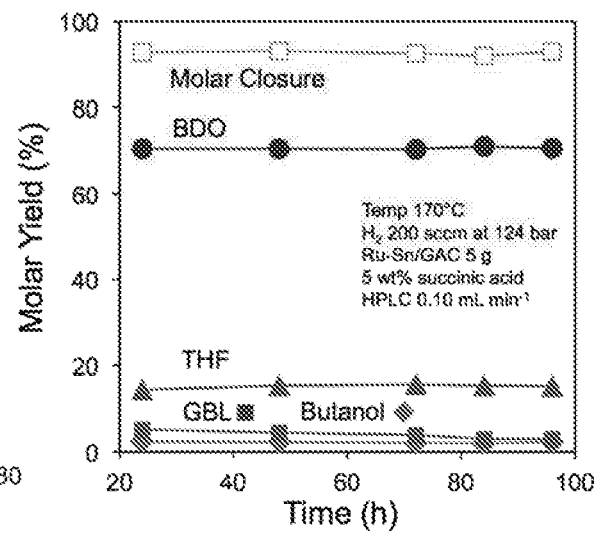
FIG. 15B illustrates the molar yields for succinic acid hydrogenation under partial conversion conditions, according to some embodiments of the present disclosure.

Once the stainless steel reactor was silica-coated, fairly stable performance (see FIGS. 15A-15B and Table 5 above)

and material properties (see Table 3 and FIGS. 16A-16B) were observed with the Ru—Sn/GAC catalyst. Neither Ru nor Sn were detected in the reactor effluent, which supports that the metal crystallites remain strongly anchored on the AC support under acidic conditions. AC supports may be very stable in subcritical water, in contrast to $Al_2O_3$ and $SiO_2$ which may be subject to hydrolysis reactions that can result in pore collapse and deactivation. For Ru—Sn/GAC, the onset of metal crystallite agglomeration (see FIG. 16B) may be due to Ru—Sn restructuring or the formation of crystals from the deposition of Ni, Cr, and Fe (see Table 4 above).

Altering the weight hour space velocity (WHSV) allowed for studying partial and complete conversion conditions with Ru—Sn/GAC. Under partial conversion conditions (<25% molar) at a WHSV of 4.0 $h^{-1}$, the Ru—Sn/GAC catalyst displayed an apparent activation energy (62.2 kJ $mol^{-1}$) that was in line with data for monocarboxylic acid hydrogenation over Ru for acetic acid (53 kJ $mol^{-1}$) and propionic acid (68 kJ $mol^{-1}$). In order to achieve complete conversion with BDO as the primary product (71% molar yield), a significantly reduced WHSV of 0.06 $h^{-1}$ was utilized. In addition to BDO, a significant amount of THF (15% molar yield) was produced under these reaction conditions. Although THF was not the target product, it has value with numerous downstream applications for biobased solvents, polymers, and textiles.

As demonstrated in this disclosure, bimetallic Ru—Sn/GAC may facilitate the continuous aqueous phase reduction of succinic acid to BDO in high yields for prolonged time-on-stream. The overcoating of Ru with Sn dramatically impacts the catalyst affinity for $H_2$ and CO, resulting in negligible uptake by chemisorption. TPR suggested the lack of a surface Ru—Sn alloy, although further work is needed to understand the nature of the active site after synthesis and under operando conditions. With prolonged exposure to reaction conditions in a trickle bed reactor, leaching of stainless steel resulted in catalyst metal crystallite restructuring to form Ni—Sn species and required coating the reactor tube with an inert silica layer by CVD. After silica coating, stainless steel leaching was greatly reduced and the Ru—Sn/GAC catalyst displayed stable performance with an activation energy of 62.2 MJ $kg^{-1}$ under partial conversion (<25% molar) conditions. Reducing the WHSV to 0.06 $h^{-1}$ resulted in complete conversion of succinic acid and a major molar product distribution of 71% BDO and 15% THF. These results highlight the potential of Ru—Sn/AC as a bimetallic catalyst for converting succinic acid to BDO, while underscoring the need for chemically compatible metallurgy for continuous processing.

Materials and Methods:

Catalyst Synthesis:

Catalysts were loaded onto nitric acid treated Darco activated carbon powder and granular supports (Sigma Aldrich). Activated carbon powder was initially sieved to <270 mesh (53 micron) and granular pellets (30-50 mesh; 300-600 micron) were used as received. The native AC support displayed a point of zero charge of pH 7.7, which was lowered to a 3.5 by nitric acid treatment. The supports were treated with concentrated nitric acid for 12-24 hours, washed with DI water until a neutral solution pH was reached, and dried under nitrogen. Following acid treatment, the support point of zero charge was measured by adding pH-adjusted water solutions in an amount slightly above the pore volume of the support to form dense slurry. Three initial solution pH values were used (pH 4, 6, 8) and the slurry was allowed to reach equilibrium. The final slurry equilibrium pH reading was measured for each starting pH, and the average value reported as the point of zero charge.

The primary PGMs, Ru, Pt, and Pd, were loaded onto the acidified AC support via SEA using the following cationic precursors obtained from Sigma Aldrich: hexmine ruthenium(III) chloride for Ru, tetraamineplatinum(II) nitrate for Pt, and tetraaminepalladium(II) chloride monohydrate for Pd. The SEA method used is as follows: 9.6 g of acidified AC was added into a large beaker with ~300 mL of deionized water. Due to the acidic nature of the carbon support, the pH of the solution was raised to 11.5-12.0 using ammonium hydroxide to deprotonate the support. In a separate beaker, the target metal cationic precursor was added to ~150 mL of DI water. Both solutions were then combined and allowed to stir at 350 rpm for at least 2 hours. After stirring, the catalyst particles were vacuum filtered, dried, and reduced in 200 sccm of pure $H_2$ for 4 hours. Pt and Ru were reduced at 300° C., while Pd was reduced at 150° C. to minimize sintering. The filtrate was recovered and the primary metal loading process was repeated until the filtrate appeared colorless, indicating approximately complete PGM loading onto the AC support (nominally 4 wt %). Secondary oxophilic metals (e.g., Ru, Sn) were loaded onto the monometallic catalysts by incipient wetness impregnation. Sn bimetallics were prepared using tin(II) chloride (Sigma Aldrich) dissolved in a minimal amount of acetone. Re bimetallics were prepared using ammonium perrhenate dissolved in water. Precursor solutions were added dropwise with continuous manual stirring. Loaded catalysts were then dried and reduced in 200 sccm of pure $H_2$ at 350° C. for Pd—Re and at 450° C. for Sn bimetallics for at least 2 hours at temperature. All catalysts were stored under ambient conditions with air exposure following synthesis.

Catalyst Characterization:

Catalysts were characterized to determine their fresh and post reaction material properties. TEM images of the fresh and spent catalysts were collected with a Tecnai G2 20 Twin 300 kV LaB6 TEM (FEI). Catalysts were dispersed in acetone, mounted onto lacey carbon Cu grids (Ted Pella), and dried overnight in a vacuum oven prior to analysis. Chemisorption and TPR of catalyst materials were performed using an Autochem II instrument (Micrometrics). The metal surface area of Pt and Pt—Sn was determined by $H_2$ pulse, Ru and Ru—Sn by $H_2$ TPD, and Pd and Pd—Re by $H_2$—$O_2$ titration. Prior to chemisorption analysis, samples were reduced at 250° C. (2° C. $min^{-1}$, 2 hours) under flowing $H_2$ (10% in Ar, 50 sccm). For $H_2$-TPD experiments, catalysts were cooled from pretreatment conditions to 40° C. under $H_2$, purged with Ar, and then ramped to 500° C. at 30° C. $min^{-1}$. For $H_2$ pulse, CO pulse, and $H_2$—$O_2$ titration experiments, samples were cooled to a dosing temperature of 40° C. under inert flow prior to analysis. TPR experiments were performed by pretreatment under flowing inert (60° C., 1 hour) followed by ramping to 650° C. under $H_2$.

Ammonia TPD was performed on an Altamira Instruments AMI-390 system. Catalyst samples (~100-200 mg) were packed into a quartz tube and heated to 450° C. at 10° C. $min^{-1}$ in 5% $H_2$/Ar flowing at 25 sccm and held for 1 hour to pre-treat the catalyst. The samples were then cooled to 120° C. and flushed with 25 sccm He for 10 minutes. For the $NH_3$-treated sample, the catalyst was then saturated with ammonia by flowing 25 sccm of 10% $NH_3$/He over the samples for 30 minutes at 120° C. Excess ammonia was removed by flushing with 25 sccm He for 10 minutes. For the untreated sample this step was omitted. The samples were then heated to 600° C. in 25 sccm He at 30° C. $min^{-1}$, holding at 600° C. for 30 minutes, and the effluent was measured with a thermal conductivity detector (TCD). The TCD was calibrated after each experiment by introducing seven pulses of 10% $NH_3$/He from a 5-mL sample loop into a stream of 25 sccm He.

Pyridine DRIFTS was performed using a Thermo Nicolet iS50 FT-IR spectrometer operating at 4 $cm^{-1}$ resolution equipped a Harrick Praying Mantis controlled-environment chamber and KBr windows. Fresh catalyst samples (~50 mg) were loaded into the chamber and pre-treated by heating in $H_2$ (5% in $N_2$, 100 sccm) with a ramp rate of 10° C. $min^{-1}$ to 160° C. and held at this temperature for 1 hour, then cooled to 50° C. and purged with 100 sccm $N_2$. A background spectrum was then collected of the clean catalyst surface before pyridine vapour was introduced by bubbling 100 sccm $N_2$ through liquid pyridine and through the catalyst bed for 30 min. The pyridine-saturated surface was then purged with 100 sccm $N_2$ for 10 minutes to remove weakly bound pyridine at 50° C. The same pretreatment procedure was used for both Ru/PAC and Ru—Sn/PAC. A spectrum was then collected of the pyridine-modified catalyst.

Catalytic Testing:

For succinic acid hydrogenation reactions, batch reactor screening experiments were performed in a Parr Multi-batch reactor system (Parr Instrument Company). Reagents, powder catalyst, and magnetic stir bars were added to 75-mL reactor cups, followed by purging and flushing of the system with pressurized He for three cycles to remove ambient air. The reactors were pressurized with $H_2$ and stirring was applied at 800 rpm. The reactors were then heated to the desired reaction temperature over a period of ~30 min. Reactors were quenched in a room temperature water bath to terminate the reaction. Products were vacuum filtered over 0.2-micron polyethersulfone membranes to remove the catalyst. Post-reaction catalysts were dried at 110° C. overnight in air for further characterization.

Trickle-bed reactor experiments were performed in a Parr tubular reactor system (Parr Instrument Company). The reactor was outfitted with nitrogen and hydrogen mass flow controllers (Brooks), a HPLC pump (Series III Scientific Instrument), tube-in-tube heat exchanger to cool the reactor products, 1-L stainless steel knockout pot with bottom sampling valve, and a solenoid-controlled backpressure regulator (Tescom). A down flow configuration was used with gas and liquid reagents fed to through the top of a 32" long, ¼" inner diameter stainless steel reaction tube. The tube temperature was monitored and controlled using an internal thermocouple centered in the catalyst bed and three furnace wall thermocouples. The tube was packed halfway with inert 1-mm glass beads (Sigma Aldrich) held in place with quartz wool (Quartz Scientific Inc.). The bed was then packed at tube mid-height with 30-60 mesh granular catalyst. The remaining void space was filled with inert glass beads held in place with quartz wool. The reactor was then sealed, loaded onto the system, pressurized with nitrogen and then heated to reaction temperature. Once at reaction pressure and temperature gas flow was switched to hydrogen and liquid flow was introduced. Continuous succinic acid reduction reactions were performed with hydrogen supplied at 200 sccm and a system pressure maintained at 124 bar. The catalyst bed temperature was varied from 165-195° C., as indicated. The mobile phase consisted of commercial succinic acid (TCI Chemicals, >99% pure) dissolved in DI water at 5 wt. %. The mobile phase was delivered at a flow rate ranging from 0.10-0.25 mL $min^{-1}$. Liquid reactor effluent samples collected from the knockout pot were syringe-filtered, and analyzed by HPLC and GC-MS, as described below. Periodically, the liquid filtrate was analyzed by ICP-IMS to detect catalyst metal leaching. After testing, the reactor was cooled to room temperature, depressurized, and ~500 mL of DI water was flushed through the catalyst bed, followed by drying under 200 sccm $N_2$. The catalyst bed packing solids were then sieved between 30-50 mesh (300-600 micron) to recover the spent catalyst granules for further analysis.

For propionic acid hydrogenation reactions, batch reactor catalyst screening experiments were performed in a Parr Multi-batch reactor system described above (Parr Instrument Company). Powder catalyst and reaction solution (20 mL of 2.5 wt % aqueous propionic acid) were loaded into the reactors with magnetic stir bars, sealed, and purged with pressurized helium three times to remove ambient air. The reactors were then pressurized to 100 bar of $H_2$ and heated to 160° C. with stirring applied at 800 rpm. After 15 hours at temperature the reactors were quenched in a room temperature water bath, cooled to room temperature, and the product solutions were filtered over 0.2-micron polyethersulfone membranes to remove the catalyst. Post-reaction catalysts were dried at 110° C. overnight in air for further characterization.

Trickle-bed flow reactor propionic acid hydrogenation reactions were performed in a Parr tubular reactor system (Parr Instrument Company). The reactor was outfitted with nitrogen and hydrogen mass flow controllers (Brooks), a HPLC pump (Series III Scientific Instrument), tube-in-tube heat exchanger to cool the reactor products, 1-L stainless steel knockout pot with bottom sampling valve, and a solenoid-controlled backpressure regulator (Tescom). A down flow configuration was used with gas and liquid reagents fed to through the top of a 32" long, ¼" inner diameter stainless steel reaction tube. The tube temperature was monitored and controlled using an internal thermocouple centered in the catalyst bed and three furnace wall thermocouples. The tube was packed halfway with inert 3-mm borosilicate glass beads (Sigma Aldrich) held in place with quartz wool (Quartz Scientific Inc.). The bed was then packed at tube mid-height with 30-60 mesh granular catalyst. The remaining void space was filled with inert glass beads held in place with quartz wool. The reactor was then sealed, loaded onto the system, pressurized with nitrogen and then heated to reaction temperature. Once at reaction pressure and temperature gas flow was switched to hydrogen and liquid flow was introduced. Continuous propionic acid reduction reactions were performed with hydrogen supplied at 200 sccm and a system pressure maintained at 100 bar. The catalyst bed temperature was 160° C., as indicated. The mobile phase consisted of commercial propionic acid (Sigma-Aldrich) dissolved in DI water at 2.5 wt. %. The mobile phase was delivered at a flow rate ranging from 0.2 mL $min^{-1}$. Reactor effluent was collected periodically for analysis. Liquid reaction products for both batch and flow experiments were analyzed by HPLC. For propionic acid hydrogenation, the only compounds detected were propionic acid and 1-propanol, there were no peaks suggesting formation of any other condensed product (e.g. ethanol or 2-propanol). After testing, the reactor was cooled to room temperature, depressurized, and ~500 mL of DI water was flushed through the catalyst bed, followed by drying under 200 sccm $N_2$.

Chemical Analysis:

For batch and trickle-bed reactor runs, molar conversion was reported as moles of substrate reacted divided by the moles of substrate introduced to the reactor. Molar selectivity was reported as moles of target product divided by moles of substrate reacted. Molar yield is defined as molar conversion multiplied by molar selectivity.

Concentrations of succinic acid, BDO, GBL, THF, butanol, and propanol were determined by HPLC on an Agilent 1100 series system (Agilent USA) utilizing a Bio-Rad Aminex HPX-87H column and cation H+ guard cartridge (Bio-Rad Laboratories) operating at 55° C. Dilute sulfuric acid (0.01 N) was used as the isocratic mobile phase at a flow rate of 0.6 mL min$^{-1}$. A refractive index detector was used for compound detection and held at 55° C. Samples and standards were injected at a volume of 20 microliters. Concentration for the analytes of interest was achieved with 7 standard calibration levels ranging from 0.05-20 mg mL$^{-1}$, with a correlation of r$^2$=0.995 or better for the calibration curve. Products were identified by co-elution at the same retention time with pure compounds, as well as confirmation by gas chromatography mass spectroscopy (GC-MS).

Concentrations of propionic acid and 1-propanol were determined by HPLC on an Agilent 1100 series system (Agilent USA) equipped with a Bio-Rad Aminex HPX-87H column and cation H+ guard column, operating at 85° C., a refractive index detector, with dilute sulfuric acid (0.01 N) as the mobile phase at 1.0 mL min$^{-1}$. Reactant and product concentrations were measured using authentic calibration standards prior to each use of the HPLC.

For GC-MS, samples were analyzed using an Agilent 6890A GC equipped with a 5973 mass spectrometer detector (Agilent Technologies) operating in splitless mode. The GC was outfitted with an Agilent DB-Wax column (30 m×0.25-mm id, 0.25-micron film), and helium (0.8 mL min$^{-1}$ column flow) was used as the carrier gas at 1 mL min$^{-1}$. The injector volume was set to 1 microliter using an Agilent autosampler. The GC-MS method consisted of a front inlet temperature of 260° C., MS transfer line temperature of 260° C., and scan range from 25 m/z to 450 m/z. A starting temperature of 35° C. was held for 3 minutes and then ramped at 15° C. min$^{-1}$ to a temperature of 250° C. and held for 5 min. The MS was set up with a solvent delay of 2.5 minutes to collect data after the solvent peak had eluted. HP MSD Chemstation software (Agilent) equipped with NIST11 database Rev. 2.0G (May 19, 2011 build) was used to identify compounds within the samples.

Figure 17:
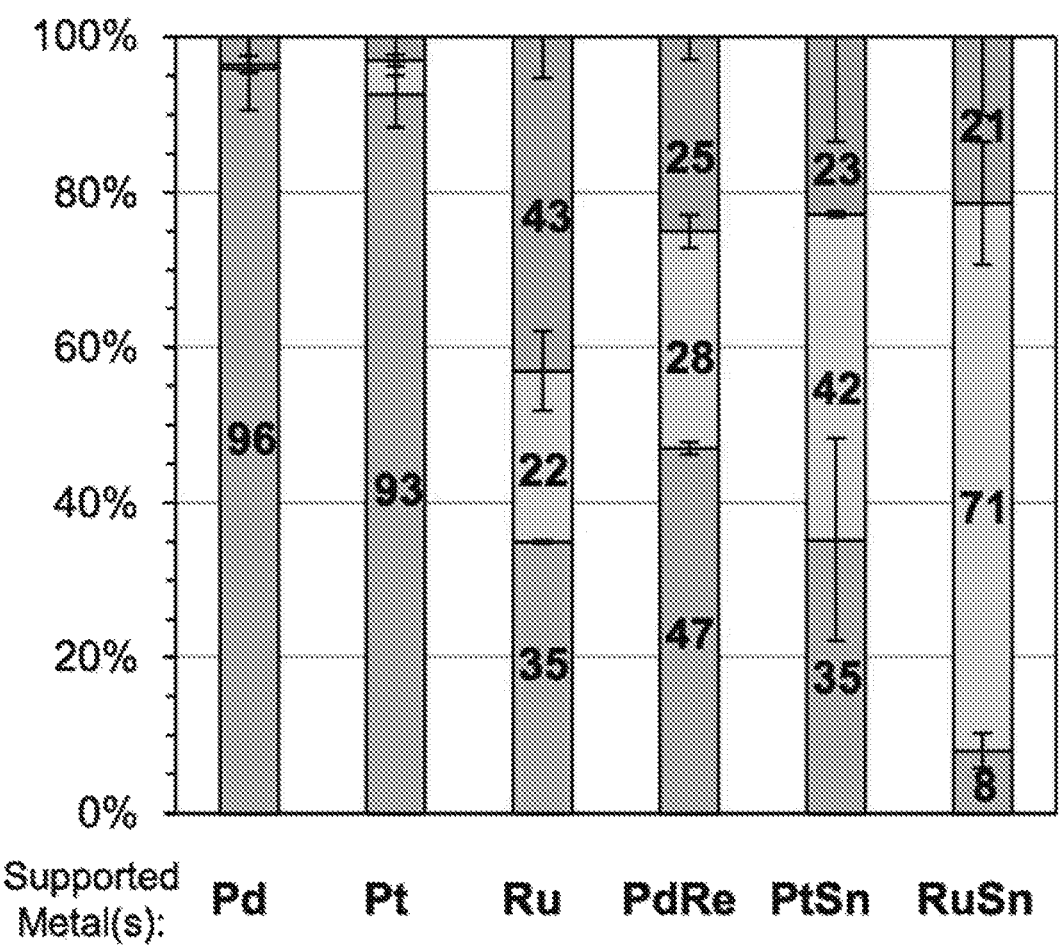
FIG. 17 illustrates data from monometallic and bimetallic powder catalyst batch reactor screening studies for the reduction of propionic acid, according to some embodiments of the present disclosure. Legend: propionic acid (blue), 1-propanol (green), lost products not detected by HPLC (red). The overlaid number gives the molar percentage of each component. Reaction conditions were as follows: 20 mL of 2.5 wt. % propionic acid in DI water, 100 mg of catalyst, 100 bar of hydrogen initially loaded at 24° C., stirring 800 rpm, temperature 160° C., reaction time 15 h.

Propionic Acid Hydrogenation Results:

The monometallic catalysts are much less effective than bimetallic catalysts for propionic acid hydrogenation, with Ru—Sn/PAC giving the highest yields of 1-propanol. The results from batch reactor catalyst screening are shown in FIG. 17. The monometallic catalysts Pd/PAC and Pt/PAC are largely unreactive for propionic acid hydrogenation with >90% of the starting propionic acid still present after 15 hours of reaction. Ru/PAC is moderately reactive with only 35% propionic acid remaining; however, the major reaction products from Ru/PAC are not detected by HPLC quantification, consisting of light products such as propane, ethane, methane, and CO$_2$, and only 22% 1-propanol is produced. Bimetallic Pd—Re/PAC and Pt—Sn/PAC catalysts are more effective in production 1-propanol, yielding 28% and 42%, respectively. Bimetallic Ru—Sn/PAC is the most effective catalyst for 1-propanol production, yielding 71% with only 8% propionic acid remaining and 21% loss. High propionic acid conversion and selectivity towards 1-propanol made the Ru—Sn/PAC catalyst an attractive catalyst to study further in a flow reactor.

Figure 18A:
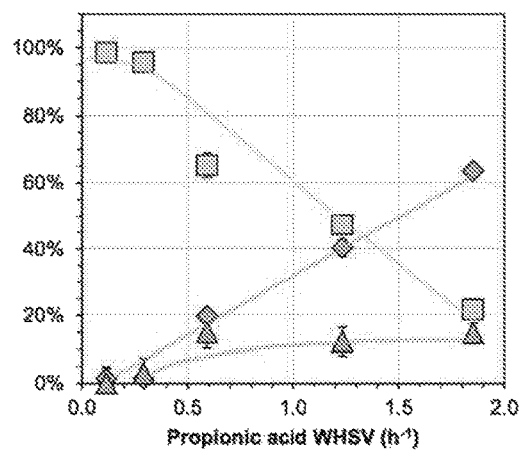
FIG. 18A illustrates trickle-bed reactor reactivity vs. WHSV using a silica-coated stainless steel reactor tube for the complete conversion hydrogenation of propionic acid using Ru—Sn/GAC (1.0:1.0), according to some embodiments of the present disclosure.

Propionic acid conversion and selectivity to 1-propanol in a packed-bed reactor with Ru—Sn/GAC were examined as a function of propionic acid weight hourly space velocity (WHSV), results are shown in FIG. 18A. Conversion of propionic acid and yields of 1-propanol are inversely proportional to WHSV, as expected with a longer residence time within the catalyst bed. The maximum 1-propanol yields were even higher for Ru—Sn/GAC in continuous flow reactions than what was observed for Ru—Sn/PAC screened in batch reactors, reaching 98±2% at a WHSV of 0.12 h$^{-1}$. At low WHSV, 0.12 to 0.3 h−1, loss of substrate to light products was observed, with losses of 0.1±5% to 3±4%, respectively. The amount of loss increased at higher WHSV, leveling out at an average of 14±4%.

Figure 18B:
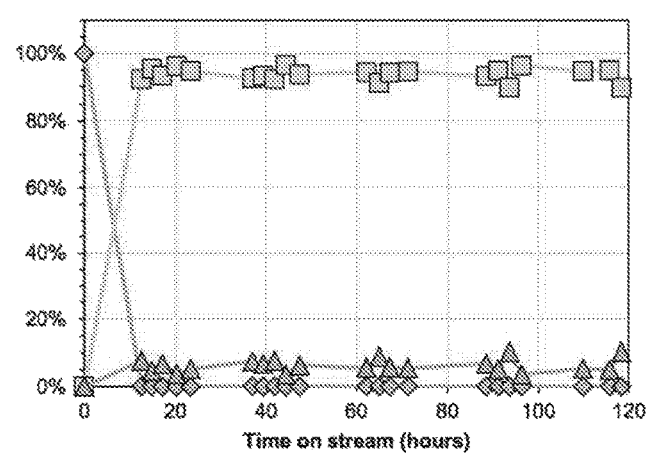
FIG. 18B illustrates trickle-bed reactor extended time-on-stream conversion of propionic acid, according to some embodiments of the present disclosure.

A long time-on-stream (TOS) run at high propionic acid conversion using Ru—Sn/GAC demonstrates remarkable 1-propanol yields and a very stable catalyst, as shown FIG. 18B. A WHSV of 0.3 h$^{-1}$ was chosen for the long TOS run due to the high yields previously observed (as shown in FIG. 18A). The long TOS run revealed a stable catalyst at these conditions with very little variation in performance for up to 120 hours on stream, with 100% conversion of propionic acid, 94±2% 1-propanol yields, and losses of 6±2%. The Ru—Sn/GAC in flow reactions greatly outperformed Ru—Sn/PAC in batch reactions, with higher selectivity to the desired product and less C—C bond scission.

Figure 19A:
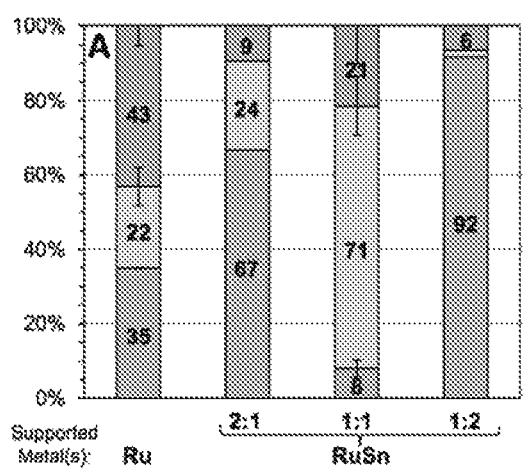
FIG. 19A illustrates a comparison of Ru/PAC and Ru—Sn/PAC using as-made catalysts at varying Ru:Sn ratios for propionic acid hydrogenation, according to some embodiments of the present disclosure.

To better understand the role of Sn in the Ru—Sn/PAC catalyst, batch reactions were performed on Ru—Sn/PAC catalysts at different Ru:Sn ratios and for Ru/PAC and Ru—Sn/PAC catalysts that had been treated with phenylphosphonic acid (PPA). The propionic acid hydrogenation performances of Ru—Sn/PAC catalysts with different Ru:Sn ratios are shown in FIG. 19A. Yields of 1-propanol were 22% for Ru/PAC, 24% for Ru—Sn/PAC (1.0:0.5), 71% for Ru—Sn/PAC (1.0:1.0), and only 2% for Ru—Sn/PAC (1.0:2.0). The selectivity of 1-propanol ($Y_{1\text{-}propanol}/[Y_{1\text{-}propanol}+Y_{loss\ product}]$) is 34% for Ru/PAC, 72% for Ru—Sn/PAC (1.0:0.5), 77% for Ru—Sn/PAC (1.0:1.0), and 22% for Ru—Sn/PAC (1.0:2.0), showing a trend across all catalysts similar to 1-propanol yields. The best catalyst in terms of 1-propanol yield and selectivity was Ru—Sn/PAC (1.0:1.0). Small addition of Sn to Ru/PAC catalyst, as in Ru—Sn/PAC (1.0:0.5), leads to 1-propanol yield and selectivity between the yields and selectivities observed for Ru/PAC and Ru—Sn/PAC (1.0:1.0), indicating some formation of the desired RuSn phase, though not to the extent of the 1.0:1.0 catalyst. Addition of too much Sn to Ru/PAC, as in the case of Ru—Sn/PAC (1.0:2.0), leads to almost no reactivity. For completeness, Sn/PAC was also tested for propionic acid hydrogenation and no reaction was observed. It appears that Ru—Sn/PAC (1.0:2.0) is similar in performance to Sn/PAC, with no effective hydrogenating surface. The sequential manner in which the catalysts were synthesized suggests that over addition of Sn will covers the Ru surface, thus preventing access to the metal that is capable of H$_2$ adsorption and dissociation.

Figure 19B:
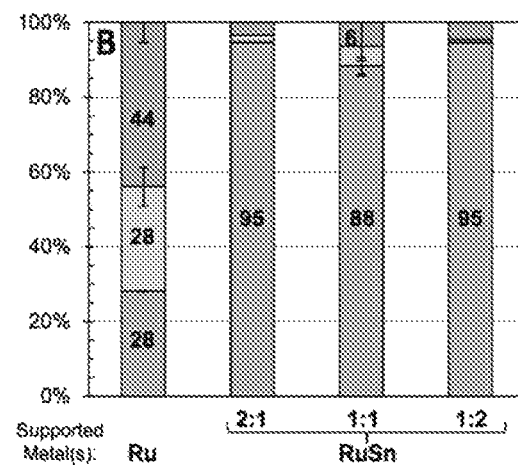
FIG. 19B illustrates a comparison of Ru/PAC and Ru—Sn/PAC using PPA-treated catalysts at varying Ru:Sn ratios for propionic acid hydrogenation, according to some embodiments of the present disclosure.

Treatment of the catalysts with PPA suppressed activity on all Ru—Sn/PAC catalysts, while the monometallic Ru/PAC catalyst was unaffected, as shown in FIG. 19B. Previous work has shown that PPA selectively binds irreversibly to Lewis-acidic oxides, and that phosphonic acids will form self-assembled monolayers on SnO$_2$. It is apparent that PPA does not bind irreversibly to Ru during PPA treatment, as propionic acid hydrogenation is nearly identical on both as-made and PPA-treated Ru/PAC. For Ru—Sn/PAC catalysts. This result suggests that the surfaces of Ru—Sn/PAC catalysts are greatly enriched with Sn oxide at the time of PPA treatment (i.e. having been exposed to air). These results also indicate that formation of a PPA-modified surface prevents the formation of an active catalyst surface, similar in activity to both Sn/PAC and Ru—Sn/PAC (1.0:2.0).

Active Site Characterization:

Monometallic Ru/PAC and bimetallic Ru—Sn/PAC catalysts were examined via controlled-atmosphere EXAFS at both Ru and Sn K edges to gain a better understanding of the catalyst structure under reaction-like conditions. Abridged EXAFS data are given in Table 7 below. Treatment of all catalysts in $H_2$ at 160° C., whether containing Sn, PPA, or neither, results in full reduction of Ru to $Ru^0$. Exposure to air leads to Ru oxidation and formation of an oxide with an average oxidation state of 3+. The estimated $Ru^0$ nanoparticle sizes for the fully reduced samples were quite small, ranging from 2.0 to 3.5 nm.

TABLE 7

Results from EXAFS experiments on Ru/PAC and Ru—Sn/PAC catalysts.

| Sample | Treatment | Oxidation State Ru | Estimated Size Sn | (nm) | $N_{Ru-Ru}$ | $N_{Sn-O}$ |
|---|---|---|---|---|---|---|
| Ru/C | 160° C., $H_2$ | 0 | — | 2.5 | 7.4 | — |
| RuSn/C | 160° C., $H_2$ | 0 | 0/4+ | 3.0 | 7.9 | 2.5 |
| Ru/C, spent | Air, RT | 3+ | — | — | — | — |
| RuSn/C, spent | Air, RT | 3+ | 4+ | — | — | 6.0 |
| Ru/C + PPA | 160° C., $H_2$ | 0 | — | 3.5 | 8.7 | — |
| RuSn/C + PPA | 160° C., $H_2$ | 0 | 0/4+ | 2.0 | 6.6 | 3.6 |

Figure 20A:
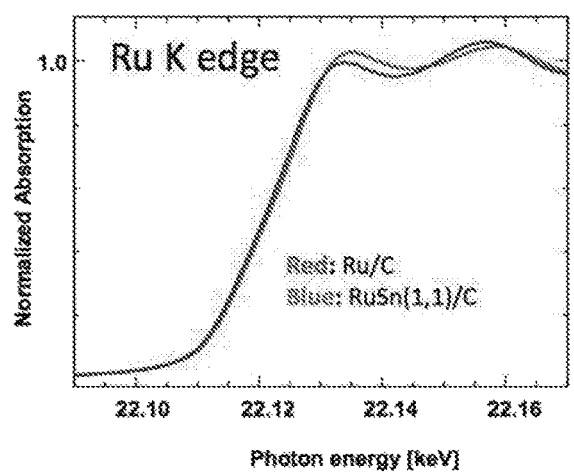
FIG. 20A illustrates Ru K edge spectra of Ru/PAC and Ru—Sn/PAC catalysts after treatment in $H_2$ at 160° C., according to some embodiments of the present disclosure.
Figure 20B:
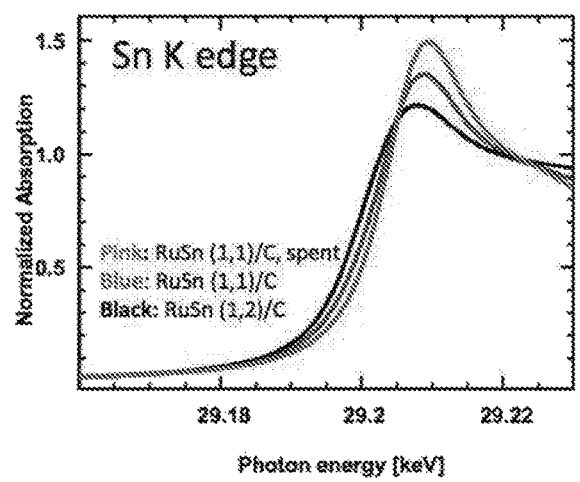
FIG. 20B illustrates Sn K edge spectra of Ru/PAC and Ru—Sn/PAC catalysts after treatment in $H_2$ at 160° C., according to some embodiments of the present disclosure.
Figure 21A:
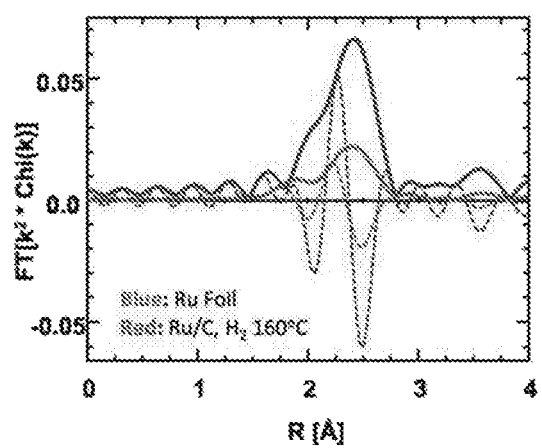
FIGS. 21A-21B illustrate Ru $k^2$-weighted Fourier transformed spectra for Ru foil standard and $H_2$-treated Ru/PAC (FIG. 21A) and $H_2$-treated and air-exposed Ru—Sn/PAC (FIG. 21B), according to some embodiments of the present disclosure.
Figure 21B:
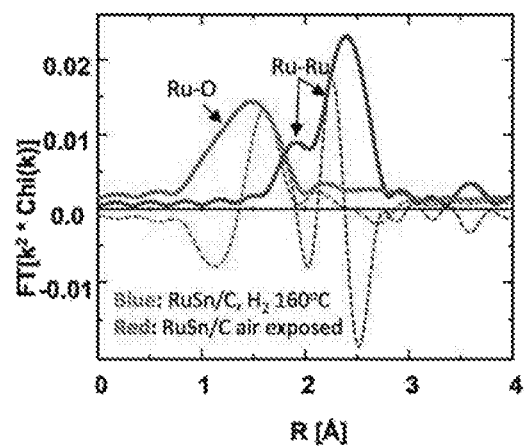
Figure 22:
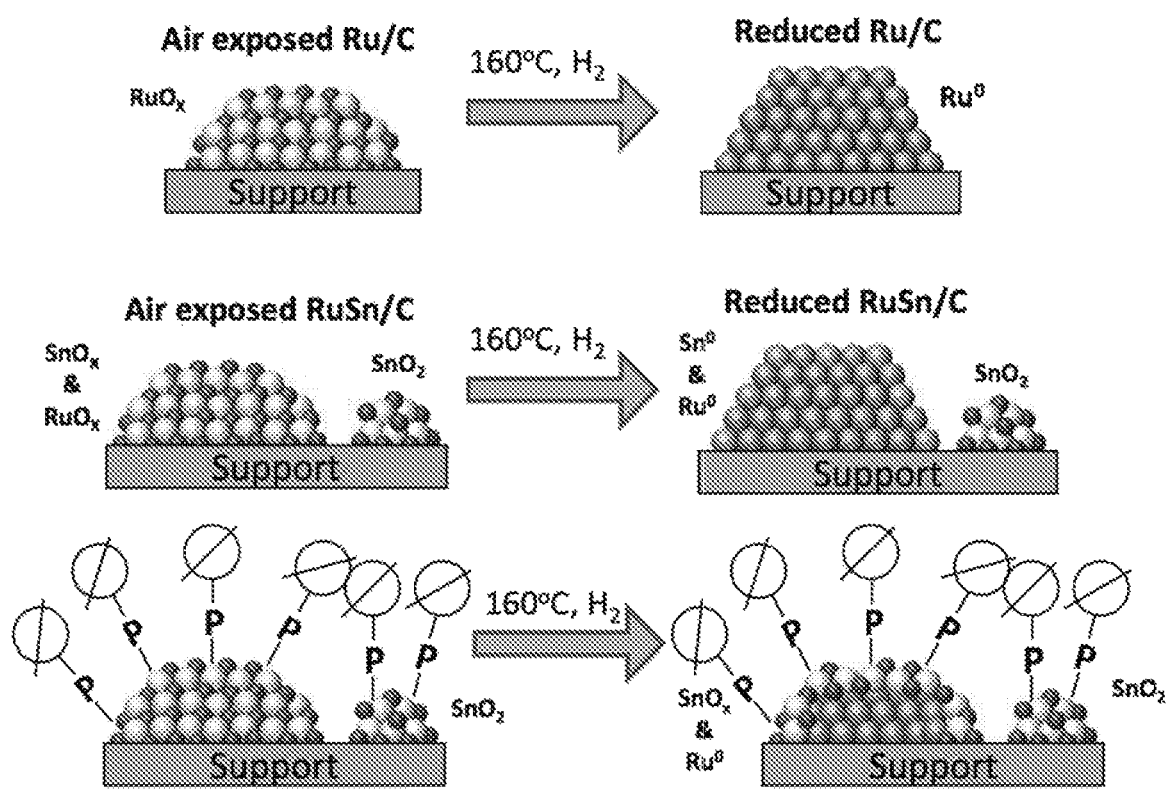
FIG. 22 illustrates evolution of the Ru/PAC, Ru—Sn/PAC, and PPA-modified Ru—Sn/PAC surfaces from as-made to $H_2$-treated catalysts, based on evidence from EXAFS and PPA poisoning experiments according to some embodiments of the present disclosure.

Ru and Sn K edge spectra for Ru/PAC and Ru—Sn/PAC catalysts are shown in FIG. 20A and FIG. 20B, respectively, while $k^2$-weighted Fourier transform spectra are shown in FIG. 21A and FIG. 21B. The inflection point in the Ru XANES region (the edge energy) for Ru—Sn/PAC is very similar to that of Ru/PAC, however, the shape of the edge is shifted to slightly lower energy and white line is also slightly lower, similar to the spectra of a $Ru_3Sn_7$ standard (not shown). This indicates that addition of Sn to Ru/PAC leads to the formation of a RuSn bimetallic nanoparticle. Direct evidence for this formation is difficult to observe by EXAFS analysis, since Ru and Sn have similar number of electrons and scatter similarly. The nearly identical edge energy of the Ru/PAC and Ru—Sn/PAC catalysts suggests that most of the Ru is present as Ru nanoparticle, meaning the bimetallic RuSn phase is likely just at the nanoparticle surface. The air-exposed Ru—Sn/PAC shows Ru in a fully oxidized state, with only Ru—O scattering and no Ru—Ru or Ru—Sn scattering observable in the EXAFS analysis (see FIG. 21B). The Ru—Sn/PAC treated in $H_2$ at 160° C. has lower white line intensity and Sn—O coordination number (N=2.5) than the air-exposed catalyst or the $SnO_2$ standard (N=6.0), indicating that some Sn is present as $Sn^0$. These factors may indicate that the Ru—Sn/PAC catalyst treated in $H_2$ at 160° C. contains Sn in oxidation states of 0 and 4+. The PPA-modified materials retain a fully reduced Ru phase, which strongly suggests that the PPA is binding to the SnOx-enriched surface and blocking access to $Ru^0$ sites. These results suggest that the active hydrogenation catalyst may have both surface-accessible $Ru^0$ and $Sn^0$, without a fully alloyed Ru—Sn phase. FIG. 22 summarizes these concepts.

Figure 23:
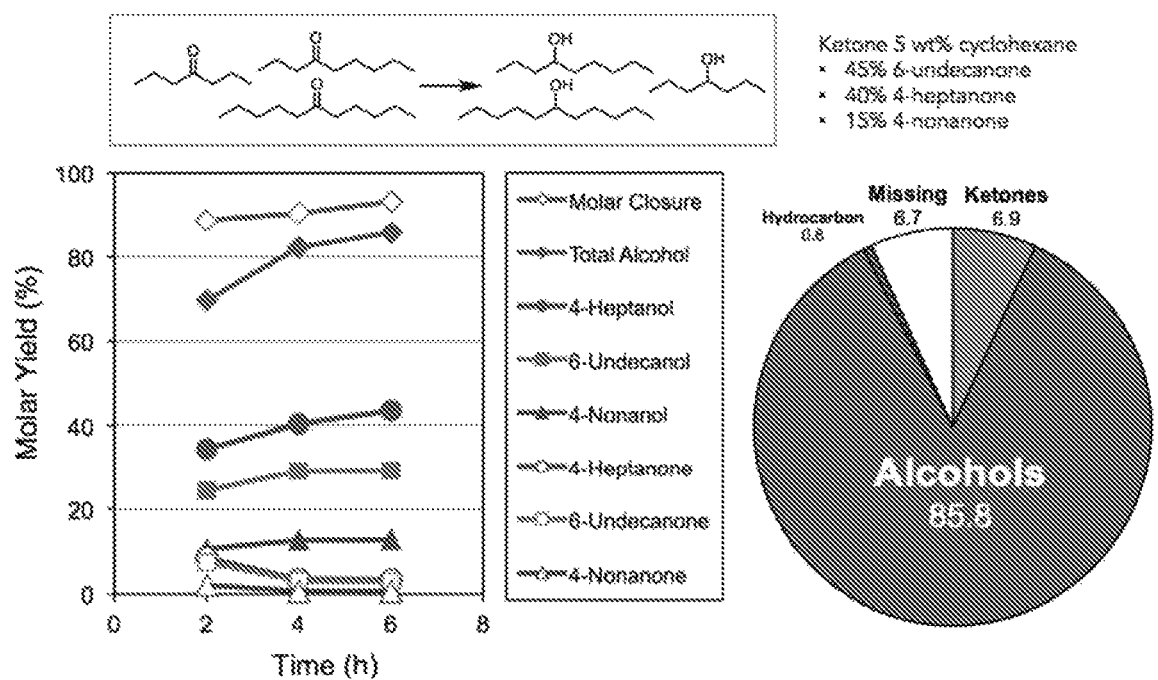
FIG. 23 illustrates experimental data obtained from the hydrogentation of various ketones to alcohols, using Ru—Sn/GAC, according to some embodiments of the present disclosure. Reaction conditions were as follows: 5 wt. % mixed ketones in cyclohexane, liquid flow rate 0.25 mL $min^{-1}$, 68 bar $H_2$ flowing at 100 sccm, 750 mg of catalyst.

Ketones to Alcohols Reaction Results:

Various ketones were reacted over solid catalysts in a packed-bed, flow-reactor. The catalyst tested was a Ru—Sn bimetallic on a GAC, solid support, at a temperature of 170° C., a pressure of about 68 bar, at a WHSV of 0.5 $hr^{-1}$. $H_2$ was co-fed at a rate of 100 sccm. Ketones tested at these conditions included 4-heptanone, 6-undecanone, and 4-nonanone, which were successfully converted to 4-heptanol, 6-undecanol, and 4-nonanol, respectively with up to 93% conversion and 86% alcohol molar yield. Results are summarized in FIG. 23.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A catalyst comprising:
   a solid support, the solid support including an oxide;
   a first metal deposited on the solid support, the first metal including at least one of ruthenium (Ru), platinum (Pt), palladium (Pd), the first metal is present at a first weight percent between about 2% and about 10%;
   a second metal deposited on the solid support such that the second metal reacts with the and first metal creating a bimetallic powder dispersed upon the solid support, the second metal including at least one of tin (Sn), rhenium (Re), cobalt (Co), molybdenum (Mo), or tungsten (W); and
   the first metal and the second metal are present in the catalyst at a first metal to second metal mass ratio between about 1.0:2.0 and about 1.0:0.5.

2. The catalyst of claim 1, wherein the first metal is Ru.

3. The catalyst of claim 1, wherein the second metal is Sn.

4. The catalyst of claim 1, wherein the second metal is present at a second weight percent between about 2% and about 10%.

5. The catalyst of claim 1, wherein the solid support has a total surface area between about 50 $m^2/g$ and about 1500 $m^2/g$.

6. The catalyst of claim 1, wherein the catalyst has an average particle size between about 10 mesh and about 400 mesh.

7. A method comprising:
   providing hydrogen;
   providing carboxylic acid;

providing a catalyst, the catalyst comprising:
- a solid support, the solid support including activated carbon and an oxide,
- a first metal deposited on the solid support, the first metal including at least one of ruthenium (Ru), platinum (Pt), palladium (Pd), the first metal is present at a first weight percent between about 2% and about 10%,
- a second metal deposited on the solid support such that the second metal reacts with the oxide and first metal creating a bimetallic powder dispersed upon the solid support, the second metal including at least one of tin (Sn), rhenium (Re), cobalt (Co), molybdenum (Mo), or tungsten (W), and
- the first metal and the second metal are present in the catalyst at a first metal to second metal mass ratio between about 1.0:2.0 and about 1.0:0.5; and contacting the hydrogen, carboxylic acid, and catalyst such that at least a portion of the carboxylic acid is converted to an alcohol.

8. The method of claim 7, wherein the carboxylic acid comprises at least one of acetic acid, propionic acid, lactic acid, succinic acid, or adipic acid.

9. The method of claim 7, wherein the alcohol comprises at least one of ethanol, 1-propanol, 1,2-propanediol, 1,4-butanediol, or 1,6-hexanediol.

10. The method of claim 7, wherein the portion is greater than 50 molar percent.

11. The method of claim 7, wherein during the step of contacting, at least a portion of the catalyst is oxidized to yield an oxidized catalyst and the oxidized catalyst converts the portion of the carboxylic acid to the alcohol.

12. The method of claim 7, wherein the step of contacting is performed in the absence of nickel (Ni) and chromium (Cr).

13. The method of claim 7, wherein the step of contacting is performed in the absence of iron (Fe).

14. The method of claim 7, wherein the step of contacting is performed using a mixture of the carboxylic acid and water.

15. The method of claim 7, wherein the catalyst is present at an average particle size between about 10 mesh and about 400 mesh.

16. The method of claim 7, wherein the contacting is performed at a temperature between about 25° C. and about 250° C.

17. The method of claim 7, wherein the contacting is performed at a pressure between about 1 bar and about 500 bar.

18. A catalyst comprising:
- a solid support, the solid support including activated carbon and an oxide;
- a first metal deposited on the solid support, the first metal including at least one of ruthenium (Ru), platinum (Pt), palladium (Pd);
- a second metal deposited on the solid support such that the second metal reacts with the oxide and first metal creating a bimetallic powder dispersed upon the solid support, the second metal including at least one of tin (Sn), rhenium (Re), cobalt (Co), molybdenum (Mo), or tungsten (W); and
- the first metal and the second metal are present in the catalyst at a first metal to second metal mass ratio between about 1.0:2.0 and about 1.0:0.5.

19. The catalyst of claim 18, wherein the first metal is Ru.

20. The catalyst of claim 18, wherein the second metal is Sn.

* * * * *